United States Patent
Starkweather et al.

(10) Patent No.: US 6,694,191 B2
(45) Date of Patent: Feb. 17, 2004

(54) AMBULATORY MEDICAL APPARATUS AND METHOD HAVING TELEMETRY MODIFIABLE CONTROL SOFTWARE

(75) Inventors: Timothy J. Starkweather, Simi Valley, CA (US); Ronald J. Lebel, Sherman Oaks, CA (US); Varaz Shahmirian, Northridge, CA (US); Philip T. Weiss, Pasadena, CA (US); David J. Marsh, Palmdale, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 278 days.

(21) Appl. No.: 09/768,201

(22) Filed: Jan. 22, 2001

(65) Prior Publication Data

US 2001/0041920 A1 Nov. 15, 2001

Related U.S. Application Data

(60) Provisional application No. 60/177,414, filed on Jan. 21, 2000.

(51) Int. Cl.$^7$ ............................................... A61N 1/00
(52) U.S. Cl. ....................................... 607/60; 604/890.1
(58) Field of Search ............................... 607/30–32, 59, 607/60; 128/903, 904; 604/891.1

(56) References Cited

U.S. PATENT DOCUMENTS

| | | | |
|---|---|---|---|
| 5,368,562 A | 11/1994 | Bloomquist et al. | |
| 5,456,692 A | 10/1995 | Smith et al. | |
| 5,630,710 A | 5/1997 | Tune et al. | |
| 5,647,854 A | 7/1997 | Olsen et al. | |
| 5,658,133 A | 8/1997 | Anderson et al. | |
| 5,658,250 A | 8/1997 | Bloomquist et al. | |
| 5,669,877 A | 9/1997 | Bloomquist | |
| 5,695,473 A | 12/1997 | Olsen | |
| 5,788,669 A | 8/1998 | Peterson | |
| 5,810,771 A | 9/1998 | Blomquist | |
| 5,876,370 A | 3/1999 | Blomquist | |
| 5,935,099 A | 8/1999 | Peterson et al. | |
| 5,935,106 A | 8/1999 | Olsen | |
| 6,024,539 A | 2/2000 | Blomquist | |
| 6,123,686 A | 9/2000 | Olsen et al. | |
| 6,208,894 B1 * | 3/2001 | Schulman et al. | 607/2 |
| 6,442,433 B1 * | 8/2002 | Linberg | 607/60 |

FOREIGN PATENT DOCUMENTS

| | | |
|---|---|---|
| WO | WO 95/02426 | 1/1995 |
| WO | WO 96/03168 | 2/1996 |

* cited by examiner

*Primary Examiner*—Jeffrey R. Jastrzab
(74) *Attorney, Agent, or Firm*—Foley & Lardner

(57) ABSTRACT

An implanted medical device (e.g. infusion pump) and handheld communication device wherein the implantable device is capable of operating under control of different software programs, wherein a first program operates after resetting the implantable device and is not capable of providing significant medical functionality but is capable of selected telemetry operations including telemetry operations that allow replacement software to be downloaded, and wherein a second program may be caused to take control of the device and is capable of significant medical functionality and selected telemetry operations but is incapable of receiving replacement software. A software image may be received in multiple messages where each message is provided with its own validation code and wherein a validation code for the whole image is provided and wherein each provided validation code must compared to a derived validation code prior to accepting the validity of the replacement software.

21 Claims, 11 Drawing Sheets

AMBULATORY MEDICAL APPARATUS AND METHOD HAVING TELEMETRY MODIFIABLE CONTROL SOFTWARE

RELATED APPLICATIONS

This application claims the benefit of prior filed U.S. Provisional Patent Application No. 60/177,414; filed Jan. 21, 2000, by Ronald J. Lebel, et al., and entitled "Medical Apparatus and Method Including an Implantable Device and an External Communication Device". The entirety of this provisional application is hereby incorporated herein by this reference, including appendices filed therewith and any references incorporated therein by reference, as if set forth in full herein.

FIELD OF THE DISCLOSURE

This invention relates generally to ambulatory medical systems that are capable of having their control software modified via telemetry including replacement of program code (i.e. algorithms) that control how variable parameters are utilized. Preferred embodiments relate to implantable infusion pumps and external devices for communicating therewith.

BACKGROUND

Various ambulatory medical devices have been proposed and a number of such devices are commercially available. These devices include implantable infusion pumps, externally carried infusion pumps, implantable pacemakers, implantable defibrillators, implantable neural stimulators, implantable physiological sensors, externally carried physiologic sensors, and the like.

Implantable infusion pumps are generally configured to accept infusion commands from an external communication device. These commands are used to set program variables that are used in defining the quantity and/or timing that is used in supplying a drug to the patient. These commands are however, typically, incapable of changing or updating the program code, i.e. algorithm(s), that utilizes these variables. As such, after manufacturing and more particularly after implantation, the operation of these devices is typically fixed and immutable with the exception of the operational variances allowed and required by a current set of values assigned to programmable variables within the device.

U.S. Pat. No. 5,360,437, entitled "Implantable Medical Device With Flexible Hardware Platform", to Thompson proposes an implantable medical device, and most particularly a pacemaker, that includes a non-volatile ferroelectric random access read/write memory for storing microprocessor instructions that can be overwritten after the pacemaker is implanted so as to allow pacemaker functionality to be modified based on progressive or otherwise changing medical condition of the patient. The '437 patent is focused on a providing a memory device that is non-volatile and that is capable of being written to.

The '437 patent fails to address several considerations associated with reliable and safe modification of control software: (1) ensuring that newly downloaded program software was not corrupted during download, (2) ensuring that the software can be downloaded in a safe manner that does not allow inappropriate operation of the implantable device during download, (3) ensuring that the downloaded software does not inadvertently overwrite any program that is associated with continued and reliable operation of the communications between the implantable device and the external communication device, (4) ensuring that upon system reset the device can be restarted in a safe mode without restarting operation of the medically active functions of the implantable device that may have become corrupted and could be dangerous to a patient, and (5) ensuring that newly downloaded software is not incompatible with any software that remains in the implantable medical device.

As such, a need exists in the field for ambulatory (e.g. implantable) devices that can not only accept updated values for variables that impact operation of the device but that can also accept modifications to its program (i.e. set of control instructions or algorithms) in a way that is safe, maintains the predictability of the software operating on the implantable device and maintains the integrity of the communication operations even if the download involves corrupted software. As such a need continues to exist in the art for implantable medical devices and communicators having enhanced reliability, enhanced functionality, and and/or enhanced safety features.

SUMMARY

It is a first object of the invention to provide an implantable medical device capable of receiving program code by telemetry from an external communication device while ensuring that newly downloaded program code was not corrupted during download.

It is a second object of the invention to provide an implantable medical device capable of receiving a software program by telemetry from an external communication device while ensuring that the downloaded program is received in a manner that does not allow inappropriate operation of the implantable device during the download.

It is a third object of the invention to provide an implantable medical device capable of receiving a software program by telemetry from an external communication device while ensuring that the downloaded code does not inadvertently overwrite any program code that is associated with continued and reliable operation of the communications between the implantable device and the external communication device.

It is a fourth object of the invention to provide an implantable medical device capable of receiving program code by telemetry from an external communication device while ensuring that upon system reset the device is restarted in a safe mode without restarting operations of medically active functions.

It is a fifth object of the invention to provide an implantable medical device capable of receiving program code by telemetry from an external communication device while ensuring that newly downloaded software is not incompatible with any medically active software that remains in the implantable device.

Other objects and advantages of various aspects of the invention will be apparent to those of skill in the art upon review of the teachings herein. The various aspects of the invention set forth below as well as other aspects of the invention not specifically set forth below but ascertained from the teachings found herein, may address the above noted objects or other objects ascertained from the teachings herein individually or in various combinations. As such, it is intended that each aspect of the invention address at least one of the above noted objects or address some other object that will be apparent to one of skill in the art from a review of the teachings herein. It is not intended that all, or even a portion of these objects, necessarily be addressed by any single aspect of the invention even though that may be the case with regard to some aspects.

A first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD processor is software controlled, and wherein the medical device includes an infusion device that is programmable to provide controlled quantities of a drug to the body of a patient and is capable of being put into a state for receiving replacement software via the MD telemetry system.

A second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes an MD memory for holding an MD program and wherein the MD processor controls operation of the medical device, at least in part, according to a program held in the MD memory, and wherein a CD memory holds an MD program that may be downloaded to the medical device and then used to control, at least in part, the operation of medical device.

In a specific variation of the second aspect of the invention the system additionally includes a second device (SD) that includes (a) an SD user readable display; (b) an SD touch-sensitive input device; (c) an SD processor and an SD memory for receiving commands from the SD touch-sensitive input device and for controlling the SD display; and (d) an SD communication system, controlled by the SD processor, for sending signals to or receiving signals from the communication device via a CD communication system within the communication device that is compatible with the SD communication system. In a further variation the SD communication system includes an infrared communication system. In a further variation the MD program within the communication device was transferred from the second device to the communication device via the SD communication system.

A third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD processor controls, at least in part, operation of the medical device according to the program held in the MD memory, wherein a CD memory holds an MD program that may be downloaded to the medical device and then used to control, at least in part, the operation of medical device, and wherein at least a portion of the messages transferable to the medical device include patient definable parameters that can be used on a regular basis to modify the treatment or monitoring performed by the medical device.

A fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device further includes an MD memory for holding an MD program that controls, at least in part, operation of the medical device, wherein the medical device is capable of executing a first type of software that allows communication with the communication device and also allows medically significant operations to occur, wherein the medical device is capable of executing a second type of software that allows communication with a communication device but does not allow medically significant operations to occur.

In a specific variation of the fourth aspect of the invention the second type of software includes bootloader software that executes upon powering up or resetting the medical device.

In an additional specific variation of the fourth aspect of the invention at least one of the following is provided: (1) the medical device is capable of receiving new software of the first type from a communication device when the medical device is executing the second type of software but not when executing the first type of software, (2) the medical device is capable of receiving new software of the second type from a communication device when the medical device is executing the second type of software but not when executing the first type of software, (3) the medical device is capable of receiving a first type of telemetry communication that includes at least a first message type, when the medical device is executing the second type of software and wherein the medical device is not capable of receiving the first type of telemetry communication when executing the first type of software, or (4) the medical device is capable of receiving a second type of telemetry communication that includes at least a second message type, when the medical device is executing the first type of software and wherein the medical device is not capable of receiving the second type of telemetry communication when executing the second type of software.

A fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes an MD memory for holding an MD program, and wherein the MD processor, at least in part, controls operation of the medical device according to the program held in the MD memory, and wherein the medical device, after being reset, boots itself into an operational mode that allows telemetry communications related to down-loading an MD program.

In a specific variation of the fifth aspect of the invention after being reset, the medical device, operates in a first operational state and then in a second operational state wherein the medical device is initially placed in the first operational state that does not allow medically significant treatment or monitoring to occur and stays in that first operational state until a command from the communication device causes transfer of operation to the second state that allows medically relevant treatment to be made or monitoring activities to occur.

A sixth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes an MD memory for holding an MD program, and wherein the MD processor, at least in part, controls the operation of the medical device, at least in part, according to the program held in the MD memory, and wherein the medical device is capable of receiving a software image, or data image, that is transferred using a plurality of messages.

In a specific variation of the sixth aspect of the invention each message of the plurality is sent with a validation code that is compared to a validation code that is derived, at least in part, from information received in the message, wherein the received and derived validation codes must appropriately compare for the received message to be considered valid. In a further variation a validation code for an entire image is transmitted and compared to a validation code that is derived, at least in part, from the received and stored image, wherein the received and derived validation codes must appropriately compare for the received image to be considered valid.

A seventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes an MD memory for holding an MD program, and wherein the MD processor, at least in part, controls operation of the medical device according to the program held in the MD memory, and wherein a validation code is downloaded from the CD telemetry system, is stored in the MD memory, and is compared to a validation code that is periodically derived from at least a portion of an image forming the MD program to ascertain whether integrity of the at least portion of the image is retained Additional specific variations, provide the medical devices of each of the above aspects and above noted variations as implantable devices such as implantable infusion pumps, implantable physiological sensors, implantable stimulators, and the like, or external devices such subcutaneous delivery infusion pumps or sensors that ascertain a physiological parameter or parameters from subcutaneous tissue or from the skin of the patient. Such infusion pumps may dispense insulin, analgesics, neurological drugs, drugs for treating AIDS, drugs for treating chronic ailments or acute ailments. Sensors may be used to detect various physiological parameters such as hormone levels, insulin, pH, oxygen, other blood chemical constituent levels, and the like. The sensor may be of the electrochemical type, optical type, and may or may not be enzymatic in operation.

In even further variations of the above noted aspects, and above noted variations, one or more of the following is provided: (1) a first portion of the MD telemetry system is incorporated into the MD processor and a second portion of the MD telemetry system is external to the MD processor, (2) a first portion of the CD telemetry system is incorporated into the CD processor and a second portion of the CD telemetry system is external to the CD processor, (3) the MD processor includes an MD central processing unit and at least one other MD functional module, (4) the CD processor includes a CD central processing unit and at least one other CD functional module, (5) the MD electronic control circuitry includes at least one external MD functional module, other than a portion of the MD telemetry system, that is external to the MD processor, or (6) the CD electronic control circuitry includes at least one external CD functional module, other than a portion of the CD telemetry system, that is external to the CD processor.

Still additional aspects of the invention set forth method counterparts to the above system aspects as well as to other functional associations and relationships, and processes that have not been specifically set forth above but will be understood by those of skill in the art from a review of the teachings provided herein.

Further aspects of the invention will be understood by those of skill in the art upon reviewing the teachings herein. These other aspects of the invention may provide various combinations of the aspects presented above as well as provide other configurations, structures, functional relationships, and processes that have not been specifically set forth above.

BRIEF DESCRIPTION OF THE DRAWINGS

The above referred to objects and aspects of the present invention will be further understood from a review of the following description, drawings, and claims set forth hereafter, wherein:

FIG. 6a depicts a flow chart of a preferred implementation of downloading multiple messages that may be used when downloading images that are larger than a maximum message size; and.

DETAILED DESCRIPTION OF PREFERRED EMBODIMENTS

Figure 1A:
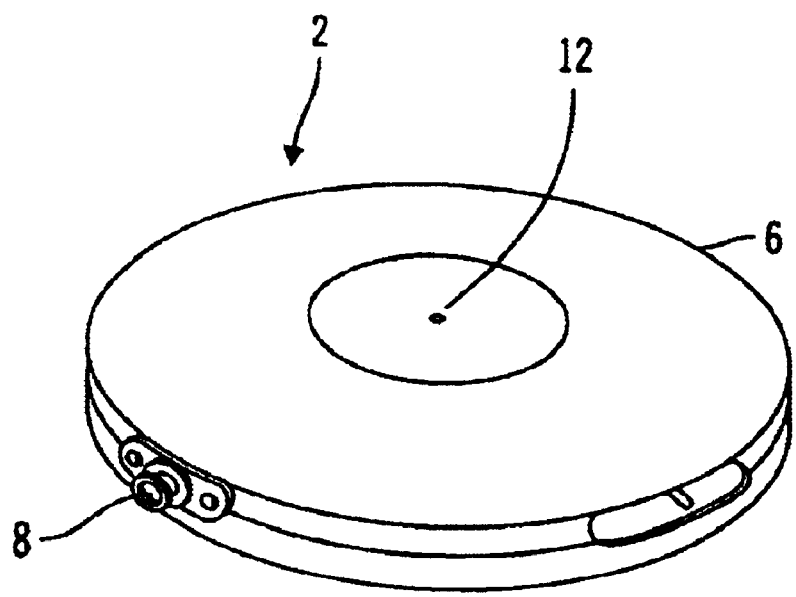
FIG. 1a depicts a depicts a perspective view of the main body of the implantable device of the first preferred embodiment.

Various details about the structural and functional configuration and operation of preferred ambulatory medical devices and preferred communication devices are found in several US patent applications filed concurrently herewith and incorporated herein by reference in their entireties: (1) Docket No. 047711-0213, (2) Docket No. 047711-0219, (3) Docket No. 047711-0220, (4) Docket No. 047711-0212, and (5) Docket No. 047711-0224.

U.S. patent application Ser. No. 09/768,202, filed on Jan. 22, 2001 (concurrently herewith), by Lebel, et at., entitled "Ambulatory Medical Apparatus and Method Using a Robust Communication Protocol", corresponding to Medtronic MiniMed, Inc.'s Docket No. 047711-0213, is hereby incorporated herein by the references as if set forth in full herein. An implanted medical device (e.g. infusion pump) and external device communicate with one another via telemetry wherein messages are transmitted under a robust communication protocol. The communication protocol gives enhanced assurance concerning the integrity of messages that impact medical operations of the implantable device. Messages are transmitted using a multipart format that includes a preamble, a frame sync, a telemetry ID, data, and a validation code. The data portion of the message includes an op-code that dictates various other elements that form part of the message. The data portion may also include additional elements such as sequence numbers, bolus numbers, and duplicate data elements. A telemetry ID for the transmitting device may be implicitly embedded in the message as part of the validation code that is sent with the message and that must be pre-known by the receiver to confirm the integrity of the received message.

U.S. patent application Ser. No. 09/768,206, filed on Jan. 22, 2001 (concurrently herewith), by Bowman, et al., entitled "Ambulatory Medical Apparatus and Method using a Telemetry System with Predefined Reception Listening Periods", corresponding to Medtronic MiniMed, Inc.'s Docket No. 047711-0219, is hereby incorporated herein by the reference as if set forth in full herein. This application provides teachings concerning an implantable medical device (e.g. infusion pump) and an external device that communicate with one another via telemetry messages that are receivable only during listening windows. Each listening window is open for a prescribed listening period and is spaced from other listening windows by an interval. The listening period is typically kept small to minimize power consumption. To increase likelihood of successful communication, the window may be forced to an open state, by use of an attention signal, in anticipation of an incoming message. To further minimize power consumption, it is desirable to minimize use of extended attention signals, and this is accomplished by the transmitter maintaining an estimate of prescribed listening start times and attempting to send messages only during listening periods. In the communication device, the estimate is updated as a result of information obtained with the reception of each message from the medical device.

U.S. patent application Ser. No. 09/768,198, filed on Jan. 22, 2001 (concurrently herewith), by Lebel, et al, entitled "Ambulatory Medical Apparatus with Hand Held Communication Device", corresponding to Medtronic MiniMed, Inc.'s Docket No. 047711-0220, is hereby incorporated herein by this reference as if set forth in full herein. This application provides teachings concerning an implantable medical device (e.g. infusion pump) and handheld communication device (CD) that exchange messages via telemetry such that commands are supplied to the implantable device and operational information is obtained therefrom. The CD is controlled, at least in part, by a processor IC according to a software program operating therein and provides feedback to a user via a visual display, an audio alarm, and a vibrational alarm, and allows input from the user via a touch sensitive keypad. Certain input functions are restricted by password. The visual display includes an icon and fixed element display region and a bitmap display region. The fixed element display region includes time and date displays, battery and drug level displays that decrement, and a moving delivery state display. Various screens allow operational or log information to be displayed and/or user entry of commands. Program features when disabled are removed from a series of screen options that can be scrolled through.

U.S. patent application Ser. No. 09/768,207, filed Jan. 22, 2001 (concurrently herewith), by Starkweather, et al., entitled "Method and Apparatus for Communicating Between an Ambulatory Medical Device and Control Device Via Telemetry Using Randomized Data', corresponding to Medtronic MiniMed, Inc.'s Docket No. 047711-0212, is hereby incorporated herein by this reference as if set forth in full herein. This application provides teachings concerning an implantable medical device (e.g. infusion pump) and handheld communication device that communicate with one another via telemetry wherein transmitted messages have enhanced numbers of and/or regularity of bit transitions to minimize the risk of synchronization loss between transmitted bits of data and received bits of data. It is taught that bit transitions for portions of messages may be enhanced by applying a pseudo-randomization scheme to those portions of messages that are transmitted in a way that allows the receiver to extract the original data from the received randomized data. Preferred randomization techniques modify (i.e. randomize) the data using a CRC value that is being accumulated while simultaneously causing the modified data to modify subsequent accumulation of the CRC itself. Upon reception, the reversal of data randomization is then made to occur so that the intended message is appropriately received.

U.S. patent application Ser. No. 09/768,221, filed on Jan. 22, 2001 (concurrently herewith), by Lebel, et al., entitled "Microprocessor Controlled Ambulatory Medical Apparatus with Hand Held Communication Device", corresponding to Medtronic MiniMed, Inc.'s Docket No. 047711-0224, is hereby incorporated herein by this reference as if set forth in full herein. This application provides teachings concerning an implantable medical device (e.g. infusion pump) and handheld communication device, wherein an implantable infusion pump possesses operational functionality that is, at least in part, controlled by software operating in two processor ICs which are configured to perform some different and some duplicate functions. The pump exchanges messages with the external communication device via telemetry. Each processor controls a different part of the drug infusion mechanism such that both processors must agree on the appropriateness of drug delivery for infusion to occur. Delivery accumulators are incremented and decremented with delivery requests and with deliveries made. When accumulated amounts reach or exceed, quantized deliverable amounts, infusion is made to occur. The accumulators are capable of being incremented by two or more independent types of delivery requests. Operational modes of the infusion device are changed automatically in view of various system errors that are trapped, various system alarm conditions that are detected, and when excess periods of time lapse between pump and external device interactions.

The first embodiment of the present invention provides a long term implantable medical delivery system that controllably supplies insulin to the body of a patient afflicted with diabetes mellitus. This embodiment includes an implantable medical device and an external communication device. In the most preferred embodiments, the communication device is a hand held device that is used directly by the patient to interact with the medical device as opposed to being limited to use by a physician, nurse, or technician. It is preferred that the communication device provide (1) the ability to send commands to the medical device, (2) receive information from the medical device, and (3) be able to present to the patient at least a portion of the information it receives from the medical device. In preferred embodiments, the patient interacts with the medical device via the communication device at least once per week, on average, more preferably at least once every other day, on average, and most preferably at least once per day, on average.

The implantable medical device (MD) includes a biocompatible housing; a reservoir within the housing for holding a quantity of insulin; a side port that attaches to the side of the housing, a catheter, that connects to the side port; a pumping mechanism, within the housing for moving the insulin from the reservoir through the sideport and through the catheter to the body of the patient; and control, monitoring, and communication electronics located within the housing. In alternative embodiments various portions of implantable medical device hardware may be located outside the housing. For example, the pumping mechanism or a telemetry antenna may be located within the sideport or other side mounted housing; or a telemetry antenna may mounted on the outside surface of the housing, or extend along the catheter.

The external communication device (CD) communicates commands to the medical device, receives information from the medical device, and communicates system status and system history to the patient. The external communication device includes a housing; a keypad mounted on the housing; a display forming part of the housing; and control, monitoring, and communication electronics located within the housing. In alternative embodiments, the keypad may be replaced in whole or in part by a touch sensitive display or a voice recognition system. In addition, or alternatively, the display may be replaced in whole or in part by a speech generation system or other audio communication system.

Figure 1B:
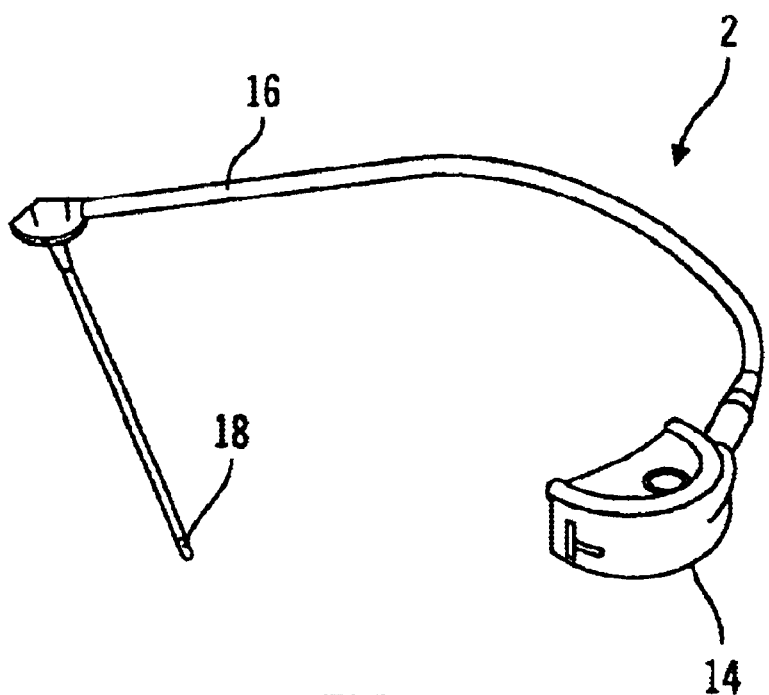
FIG. 1b depicts a perspective view of the catheter assembly that attaches to the main body of the implantable device of the first preferred embodiment.

The outer appearance of the implantable device 2 is depicted in two pieces in FIGS. 1a and 1b and includes housing 6 having a drug outlet port 8, and a refill port 12, a removable sideport 14 that mounts against the side of the housing 6 over outlet port 8, and a catheter 16 having a distal end 18 and a proximal end that attaches to sideport 14. In alternative embodiments, the implantable device may take on a different shape and/or the sideport may be removed in favor of a permanently mounted catheter assembly.

Figure 2:
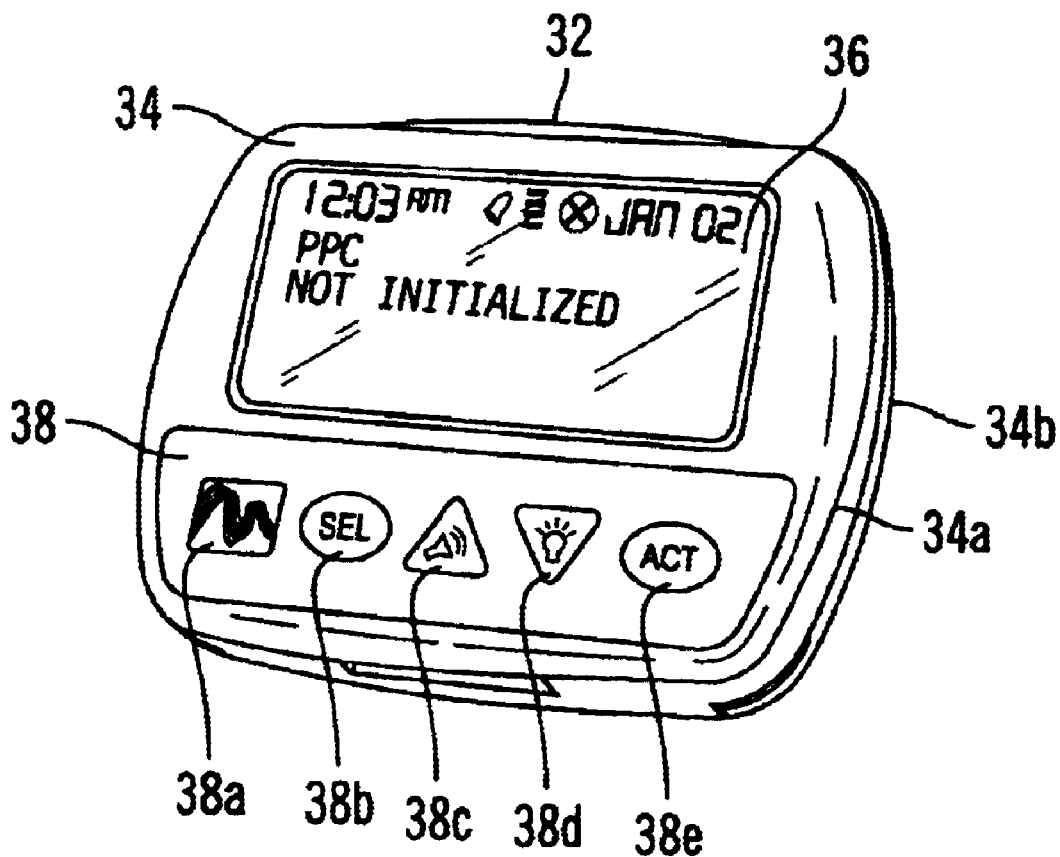
FIG. 2 depicts a perspective view of external communication device of the first preferred embodiment.

The outer appearance of the external communication device 32 is depicted in FIG. 2. The various components of the external communication device are fitted in or on housing 34. Housing 34 is divided into a front portion 34a and a back portion 34b. The front portion 34a is provided with an opening in which an LCD panel 36 is positioned. The panel 36 has a lower portion that is a bit map display and an upper portion that provides icons and fixed element displays. The front portion 34aof the external communication device is also provided with a five-element keypad 38. A first key 38a is not located under a raised pad and does not provide tactile feedback when it is touched and may be used for special functions. The remaining four keys 38b, 38c, 38d, and 38e have raised pads that provide tactile feedback when they are depressed. These remaining keys may be used in normal device operation and are known as the select key, the up arrow key, down arrow key, and the activate key, respectively. The back portion 34b of the housing is fitted with a door under which a compartment is located for holding a replaceable battery.

Figure 3:
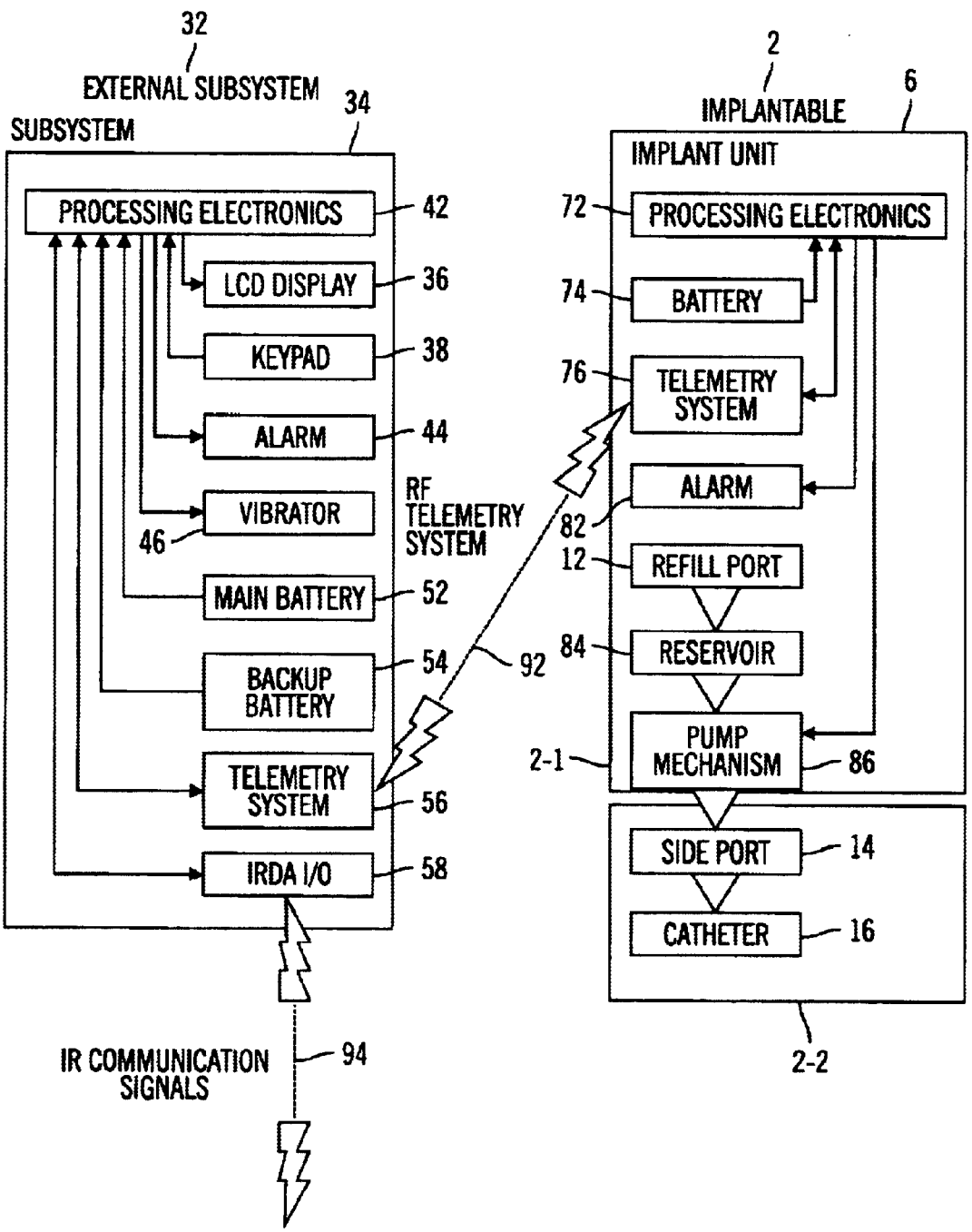
FIG. 3 depicts a block diagram of the main components/ modules of both the implantable device and the external communication device of the first preferred embodiment.

FIG. 3 depicts a simplified block diagram of various functional components or modules (i.e. single components or groups of components) included in the implantable medical device 2 and external communication device 32. The external communication device 32 includes (1) a housing or cover 34 preferably formed from a durable plastic material, (2) processing electronics 42 including a CPU and memory elements for storing control programs and operation data, (3) an LCD display 36 for providing operation for information to the user, (4) a keypad 38 for taking input from the user, (5) an audio alarm 44 for providing information to the user, (6) a vibrator 46 for providing information to the user, (7) a main battery 52 for supplying power to the device, (8) a backup battery 54 to provide memory maintenance for the device, (9) a radio frequency (RF) telemetry system 56 for sending signals to the implantable medical device and for receiving signals from the implantable medical device, and (10) an infrared (IR) input/output system 58 for communicating with a second external device.

The second external device may include input, display and programming capabilities. The second device may include a personal computer operating specialized software.

The computer may be used to manipulate the data retrieved from the communication device or the medical device or it may be used to program new parameters into the communication device or directly into the medical device, or even used to download new software to the communication device or to the medical device. The manipulation of the data may be used in generating graphical displays of the data to help aid in the interpretation of the data. Such data interpretation might be particularly useful if the medical device provides data concerning a physiological parameter of the body of the patient, such as a glucose level versus time. More particularly the computing power and display attributes of the second device might be even more useful when the medical device includes both an implanted sensor (e.g. glucose sensor), or external sensor, and an implanted pump (e.g. insulin pump), or external pump, where the second external device may be used to enhance the ability to ascertain the effectiveness of the two devices working together. Successful control periods and problem control periods could be more readily identified. In fact, if the two devices work on a closed loop basis or semi-closed loop basis, the analysis performable by the second external device may be useful in deriving new closed loop control parameters and/or in programming those parameters directly into the communication device or the medical device or devices.

The implantable device 2 includes (1) a housing or cover 6 preferably made of titanium that may or may not be coated to enhance biocompatibility, (2) processing electronics 72 including two CPUs and memory elements for storing control programs and operation data, (3) battery 74 for providing power to the system, (4) RF telemetry system 76 for sending communication signals (i.e. messages) to the external device and for receiving communication signals (i.e. messages) from the external device, (5) alarm or buzzer 82 for providing feedback to the user, (6) refill port 12 for accepting a new supply of drug as needed, (7) reservoir 84 for storing a drug for future infusion, (8) pumping mechanism 86 for forcing selected quantities of drug from the reservoir through the catheter to the body of the patient, (9) sideport 14 for providing a replaceable connection between the (10) catheter and the pump housing and for allowing diagnostic testing of the fluid handling system to occur, and catheter 16 for carrying medication from the implant location to the desired infusion location.

In this embodiment, the pump mechanism is preferably a low power, electromagnetically driven piston pump. Such as for example Model Nos. P650005 or P650009 as sold by Wilson Greatbatch Ltd. of Clarence, N.Y. which have stroke volumes of 0.5 microliters and draw under 7 mJ (e.g. about 6 mJ) per pump stroke and under 4 mJ (e.g. about 3 mJ) per pump stroke, respectively. The pump mechanism dispenses a sufficiently small volume of insulin per stroke so that a desired level of infusion resolution is achieved. For example if an infusion resolution of 0.2 units of insulin were desired when using U400 insulin, then a stroke volume of about 0.5 microliters would be appropriate. In other embodiments other types of infusion pumps may be used, e.g. peristaltic pumps.

The size of the reservoir is preferably large enough to hold sufficient insulin so that refilling does not have to occur too often. For example, it is preferred that time between refills be within the range of 1.5–4 months or longer, more preferably at least 2 months, and most preferably at least 3 months. Opposing the containment of a large volume of insulin, is the desire to keep the implantable device as small as possible. In the present embodiment the implantable device and reservoir has been designed to hold about 13 ml of insulin. A preferred insulin has a concentration of 400 units per milliliter and is available from Aventis HOE 21Ph U-400 from Aventis Pharma (formerly Hoechst Marion Roussel AG, of Frankfurt am Main, Germany). This insulin is a highly purified, semi-synthetic human insulin with 0.2% phenol as a preserving agent, glycerol as an isotonic component, TRIS as a buffer, plus zinc and Genopal® as stabilizing agents. This quantity and insulin concentration allows about 2–4 months between refills. In other embodiments higher insulin concentrations may be used (e.g. U-500 or U-1000) to increase time between refills or to allow reduction in reservoir size. In some embodiments, when higher concentrations are used, any quantized minimum delivery amounts may be reduced by modifying the pumping mechanism, control circuitry, or software so that infusion resolution is not adversely impacted.

The external communication device contains appropriate software to provide proper control of the device including appropriate functionality to allow communication with the medical device, to allow adequate control of the operation of the medical device, and to give appropriate feedback to the user regarding overall system operation. The medical device is provided with appropriate software to allow communication with the external communication device, to allow safe and appropriate operation of the medical functionality of the device, and to allow direct feedback to the user concerning device status via the internal alarm. According to selected aspects of the present invention the software program(s) within the implantable device may be replaced as needed. The replacement of software programs (i.e. application code or bootloader code) in this context is different from a mere change in program variables that may allow various control limits to be changed or even to allow the code to execute different algorithms that are preexistent within the code. The replacement of software programs in this context involves the replacement of at least portions of the code that sets forth program algorithms.

The control electronics of both the implantable device and external communication device are centered around microprocessor based integrated circuits, i.e. processor ICs, that are implemented in the present embodiment in the form of application specific integrated circuits (ASICs). In the present embodiment, the control electronics of the implantable device are centered around two identical application specific integrated circuits (ASICs) that are mounted on a hybrid circuit board. In some alternative embodiments a single ASIC may be used, or a single dual processor integrated ASIC may be used. In a single processor device one or more circuits may be provided to monitor the operation of a CPU in the processor to ensure it continues to operate properly in one or more key functions. In the single dual processor integrated ASIC, dual circuitry could be provided so that each processor could act independently of the other. In the single dual processor embodiment, a single off-circuit oscillator may be used to drive both processors or each may have an independent oscillator. A single chain of timing circuits could be used in driving both processors or independent chains of timing circuits could be used. Furthermore, if a single oscillator is used to drive both processors, then one or more separate circuits such as a counter and an RC timer may be used to verify appropriate operation of the oscillator and/or any particular timing circuit dependent thereon.

In different embodiments, more or less of the control electronics may be implemented within one or more processor ICs while any remaining portions may be implemented external to the processor ICs. The processor IC may be referred to as an MD processor if used in the medical device portion of the system or a CD processor if used in the communication device portion of the system. In other embodiments the process IC used in the communication device may be different, e.g. have a different CPU or different peripheral modules, from a processor IC used in the medical device. In embodiments where more than one processor IC is used in either the medical device or the communication device each of the processors may be different. They may be specifically designed for their intended roles when they perform at least partially different functions. Depending on particular design constraints portions of the electronics not embodied in the processor ICs may form part of one or more hybrid circuit boards or be otherwise mounted within, on, or even in some cases external to a device housing.

Each processor IC of the present embodiment includes a 16-bit core CPU which is a CMOS low power version of the INTEL 8086 processor and various peripheral modules that are used for system control, data acquisition, and interfacing with electrical components external to the processor IC. The peripheral modules of the processor IC include (1) a non-volatile memory interface module, e.g. a SEEPROM interface module, (2) a boot ROM module; (3) an SRAM module; (4) a memory decoder module; (5) a crystal oscillator module; (6) a timer module; (7) a pump interface module; (8) a watchdog module; (9) an RF module; (10) an interrupt handler module; (12) an analog-to-digital converter module; (13) an LCD clock driver module; (14) an alarm interface module; and (15) first and second synchronous serial interface modules.

In alternative embodiments fewer, additional, or different peripheral modules may be incorporated into the processor ICs. In one extreme the processor IC may simply incorporate a CPU with all other modules being external thereto. In the other extreme almost all, if not all, electronic components may be incorporated into a single processor IC. Intermediate alternatives might incorporate a single additional module into the processor IC (in addition to the CPU), others might incorporate more than one, e.g. 4 or more, 8 or more, or the like. In still other alternatives, the number of peripheral modules or components in an entire device may be considered and more than a certain percentage of them incorporated into one or more processor ICs, e.g. more than 50%, more than 75%, or even more than 90%.

The processor ICs are responsible for basic system management and communication of information between the implantable device and the external communication device through the RF telemetry link. The telemetry systems of the present embodiment are implemented in part through electrical hardware and in part through software controlled by a processor IC.

In the present embodiment, most of the required electrical modules for the implantable device are integrated within the processor ICs. However, several are not. These additional modules include two independent crystal oscillators (one for each ASIC); two non-volatile memory modules (one for each ASIC), e.g. SEEPROM chips; a volatile memory module (used only by one of the ASICs), e.g. an SRAM chip; pump driver circuitry (partially controlled by the each ASIC); front end telemetry system circuitry; and voltage measurement circuitry associated with the pump driver circuit; a buzzer; and a battery.

Within the implantable device telemetry operations are controlled by a single ASIC (sometimes known as the main processor) The other processor (sometimes known as the monitor processor) controls the buzzer and is thus responsible for audio communications coming from the implantable device. The medical functionality of the implantable device (i.e. the administration of insulin in the present embodiment) is controlled by both processors. To maintain the implantable device in a fail safe operational mode, these two processors maintain an appropriate level of agreement concerning infusion instructions an error condition results and either pumping is halted or a system reset may be made to occur. The main and monitor processors communicate with each other through the use of hardwired serial input and output ports.

As with the implantable device, the control electronics of the external communication device are centered around an ASIC that controls and interacts with a number of peripheral modules. These peripheral modules include an LCD display and driver, an IR port and driver, a crystal oscillator, a keypad and keypad interface, power management modules and reset circuitry, external volatile memory (e.g. SRAM) and non-volatile memory (e.g. SEEPROM), a buzzer, and front end telemetry hardware.

The telemetry system for the implantable device and the external communication device provide a half-duplex link between each other using a carrier frequency of about 250 kHz (e.g. about $2^{18}$ Hz) and a data signal having a frequency of about 8 kHz (e.g. about $2^{13}$). The transmitter hardware uses the 8 kHz data signal to modulate the carrier signal to generate signals that will be transmitted by the antenna. The receiver hardware receives the modulated signal and demodulates it to extract the 8 kHz data signal. Both the implantable device and the external communication device have transmit and receive capabilities to allow two-way communication.

Most of the RF telemetry circuits necessary for communication between the external communication device and the implantable device are implemented in the processor IC. In order to minimize the digital noise interference that the processor IC might impart to the weak RF signals that are being received, a high-gain RF amplifier is implemented off-chip. Also an RF antenna, that is used for both transmission and reception, and circuitry to select between reception and transmission are implemented off-chip. The remaining analog sections and all the digital demodulation circuits are implemented in the processor IC.

A Quadrature Fast Acquisition Spread Spectrum Technique (QFAST®) is used as the modulation technique. QFAST® modulation is based on an Offset Quadrature Phase Shift Keying (QPSK) modulation technique. In this technique, data generated by the CPU modulates clock signals at the carrier frequency. As a result of quadrature modulation, in-phase and quadrature-phase components of the given data stream are generated. The two components are then applied to opposite ends of the external antenna so that a combined signal is transmitted.

Further detail about QFAST® (Quadrature Fast Acquisition Spread Spectrum Technique) may be found in U.S. Pat. No. 5,559,828, entitled Transmitted Reference Spread Spectrum Communication Using a Single Carrier with Two Mutually Orthogonal Modulated Basis Vectors, by Armstrong, et al. This patent is here incorporated herein by reference as if set forth in full.

Further details about the structural and functional configuration and operation of preferred ambulatory medical devices and preferred communication devices are found in several US patent applications.

Two pieces of software may run in the implantable device at different times: (1) second stage bootloader software, and (2) application software. Upon reset, a boot program is executed by each processor IC from its internal ROM. This bootloader program in turns loads a second stage bootloader program into the RAM of each processor IC from the SEEPROMs that are attached to each, respectively. This second stage bootloader software is incapable of operating the insulin pumping mechanism, but is capable of performing limited telemetry and communication activity. One capability of the second stage bootloader software is to download new software from the External Communication Device. This download capability may be used to download new second stage bootloader software or it may be used to download new application software. The second stage bootloader software remains the active software controlling the implantable device, until a valid copy of new application software is downloaded and executed. At the time that the new application software is executed, the second stage bootloader software relinquishes control of the implantable device. The application software is the software that is capable of controlling the insulin pump as well as receiving command instructions from the external communication device concerning insulin delivery. The implantable device, when running in application mode (i.e. running the application software), ignores messages related to software downloading as these functions are not supported by the application software.

A second stage bootloader program is provided for both the main and monitor processor ICs. The SEEPROM for each of the monitor processor and the main processor contains it own unique second stage bootloader software. This software serves three primary purposes: (1) It places the medical device in a safe state where medical operations are inhibited, (2) It enables the implantable device to receive new or replacement application software via telemetry from the external communication device while the implantable device is in a non-medically active state (i.e. a safe state), and (3) It allows the system to reset itself, after the occurrence of system failure of some type, so that the implantable device may be placed in a state that allows communication with the external communication device but does not allow or even support the medical functionality of the system (i.e. the dispensing of insulin in this embodiment).

In alternative embodiments, medical operations may not be completely eliminated when the bootloader program is in control of the medical device, but instead they may be curtailed to a limited set of operations. This limited set of operations may be implemented via the CPU and based on simplified software operations, or based on hardcoded instructions, or even implemented via circuitry that functions entirely or almost entirely independent of the processor. In the independent circuitry implementation the processor may retain the ability to shut off power to the independent circuitry when application software is properly controlling the device. For example, the minimal functionality maintained may involve the ability of an infusion pump to deliver a minimal amount of drug per hour so as to reduce the risk of catheter blockages that otherwise might form. In another example, a pacemaker device might be limited to a fixed, minimum, and independently implemented pulsing rate. In a further example, physiological monitoring activities may be allowed to continue but may not be allowed to directly control closed loop infusion operations, closed loop stimulation activities, or the like, but may be allowed to produce warnings to the patient so further analysis and actions may be taken if a serious condition exist.

After power-up, both the main and monitor processors in the implantable device immediately begin executing the ROM code resident at the boot vector as described above. The execution of this ROM code places the pump hardware in a safe state, then looks for a SEEPROM attached to the respective processor IC. The code resident in the SEEPROM is then loaded into memory and executed so that control of the implantable device is handed over from the ROM code to the second stage bootloader code. For the device to become medically active, new application software must be downloaded from the external communication device as any previously held versions of the application code have been removed upon system reset or became inactive upon system reset. In alternative embodiments, in certain circumstances, re-execution of previously loaded software may be acceptable. For example if previously loaded software were held in non-volatile memory such as a SEEPROM, as is the bootloader software, that software may be reloaded into RAM from the SEEPROM along with its previously supplied validation code.

In the preferred embodiment, reset of a processor IC is made to occur by triggering the watchdog for that processor. The triggering of the watchdog may occur by self-detection of an error in the system or by receipt of a reset command by the processor. The watchdog module for each processor IC is set by software to be serviced at both interrupt and mainline level by the processor IC's CPU. This dual level servicing prevents permanent malfunction of the system that might otherwise result from the masking of interrupts at mainline level or infinite loops at either mainline or interrupt level. When an error occurs the watchdog for the affected processor is tripped and the processor is reset. The medical device is programmed so that if one of its processors is reset, the other processor will reset as a result of an inter-processor communication failure. In the medical device, when a reset command is received by the main processor (via telemetry), it forwards the reset message to the monitor processor then it and the monitor processor reset. As such when either an error occurs in one of the processors or a reset message is received both processors get reset, thus enabling both processors in the device to reboot. The triggering of the watchdog sends an alarm signal to any attached sound generation hardware (i.e. buzzer on the monitor processor for the present embodiment) so as to cause an alarm to sound. The watchdog continues to generate its alarm signal until it is reset during the boot process.

In the preferred embodiment, a boot ROM module for each IC provides the initial boot code for the CPU. The boot ROM is provided as metal mask programmable ROM. Upon booting the CPU finds the ROM located at a location consistent with the Intel 8086 specification for reset vectors. The boot-code contains a program which loads further code from a non-volatile memory module located off chip (i.e. specifically a SEEPROM in the present embodiment). When booting the processor IC, the first order of business is to initialize the essential segment registers (e.g. a data segment and stack segment registers are made to point to existing memory). Immediately thereafter, the code deactivates certain portions of the hardware including a pump fire register. Next the watchdog module is acknowledged so that any alarm signaling is stopped and so that system can again be reset if a failure occurs. The remaining boot code loads a section of code out of the SEEPROM and into the RAM at a location specified by the data in the SEEPROM itself.

The first several bytes of the SEEPROM contain memory address destination values, program packet length values, and an additive checksum that are used by the bootloader in loading software from the SEEPROM, confirming accurate loading, and executing the loaded software.

The code, as it begins to communicate with the SEEPROM, expects the SEEPROM to give periodic acknowledgements. If these acknowledgments are not received, the program assumes that the SEEPROM is not responding and sends a signal to the alarm driver so that a "No SEEPROM Acknowledge" sound may be produced if appropriate sound generation hardware is connected to the driver (e.g. the monitor processor is so connected but the main processor is not). Once the alarm sound is made, the bootloader resets the entire process in an attempt to reestablish SEEPROM communications.

Once the indicated amount of code has been loaded from the SEEPROM into the RAM beginning at the specified address, a computed checksum is compared with the checksum provided with the code stored in the SEEPROM. If the computed checksum does not match what was provided, a 'Checksum Fail' sound is made and the boot code begins the loading process again.

Provided the checksum has passed, a vector is formed by the ROM code to point to the entry point of the loaded code and a jump to that point is executed. This is performed by (1) writing five bytes to a section of reserved RAM to form an intersegment jump instruction with a destination address (both segment and offset) set to the location of the code packet that was just copied into RAM, and (2) executing, at the end of the ROM code, a jump to the location where the five bytes in step (1) were written, and then (3) executing the jump command created in step (1). As the jump instruction of step (1) was created during run time, based in part on the data that was just loaded into RAM from the SEEPROM, this is a form of self-modifying code, even though only the jump destination is modified.

The above procedure uses two jumps for several reasons. First, the location in ROM of the first jump is not modifiable, being written in ROM. The code must jump to a known location, intersegment or not. The destination of that first jump was necessarily chosen to be in RAM so that it could be modifiable based on the code destination found in the SEEPROM. As noted, the second jump statement, the one residing in RAM, is constructed by the program at run time. It is modified to reflect the desired destination (necessary for the flexibility desired in the loader) and, when executed, directs the CPU to that desired destination.

Figure 4A:
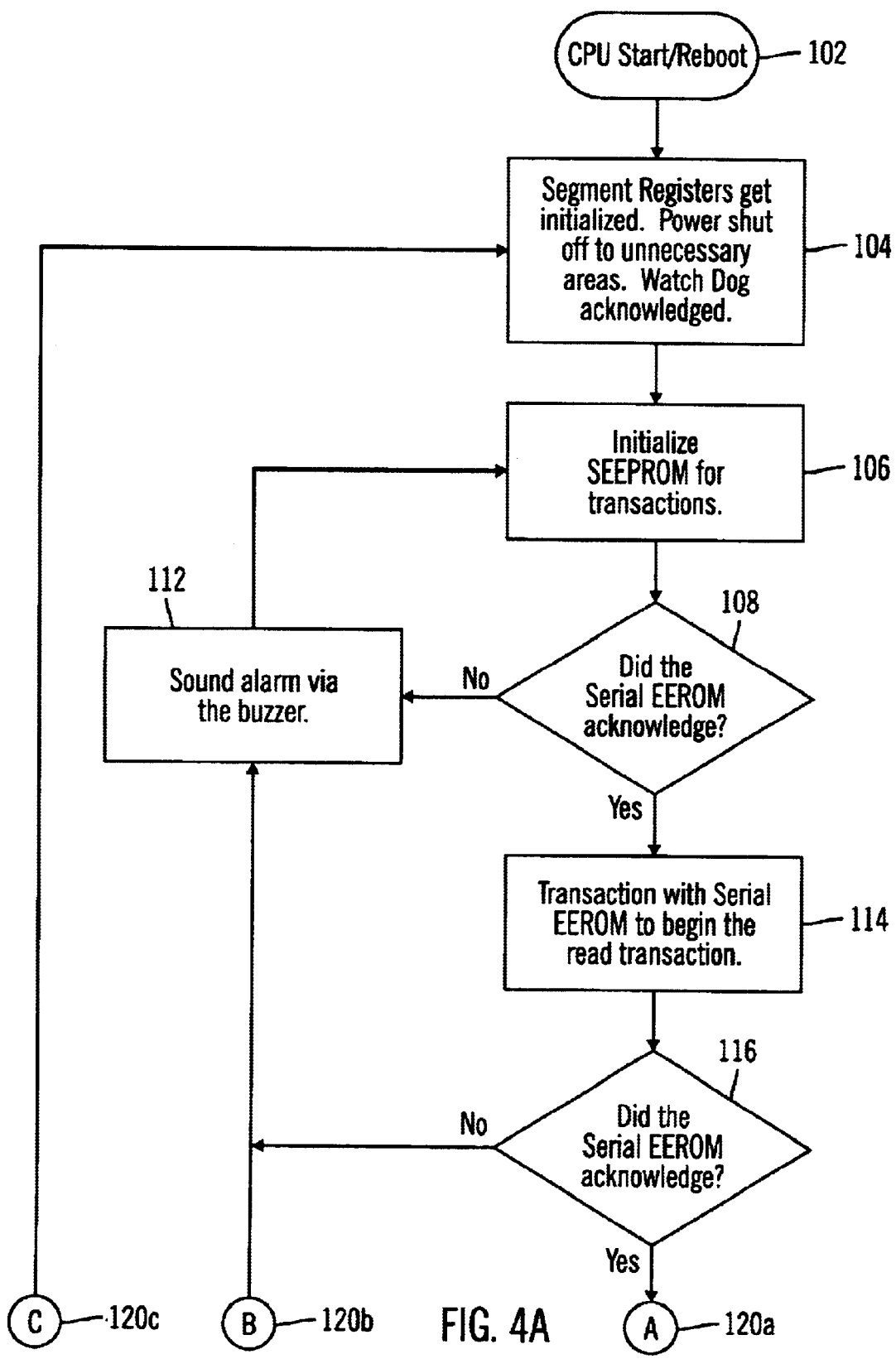
FIGS. 4a and 4b depict a flowchart of the boot procedure used in the implantable device to load the second stage bootloader software as used in the first preferred embodiment.
Figure 4B:
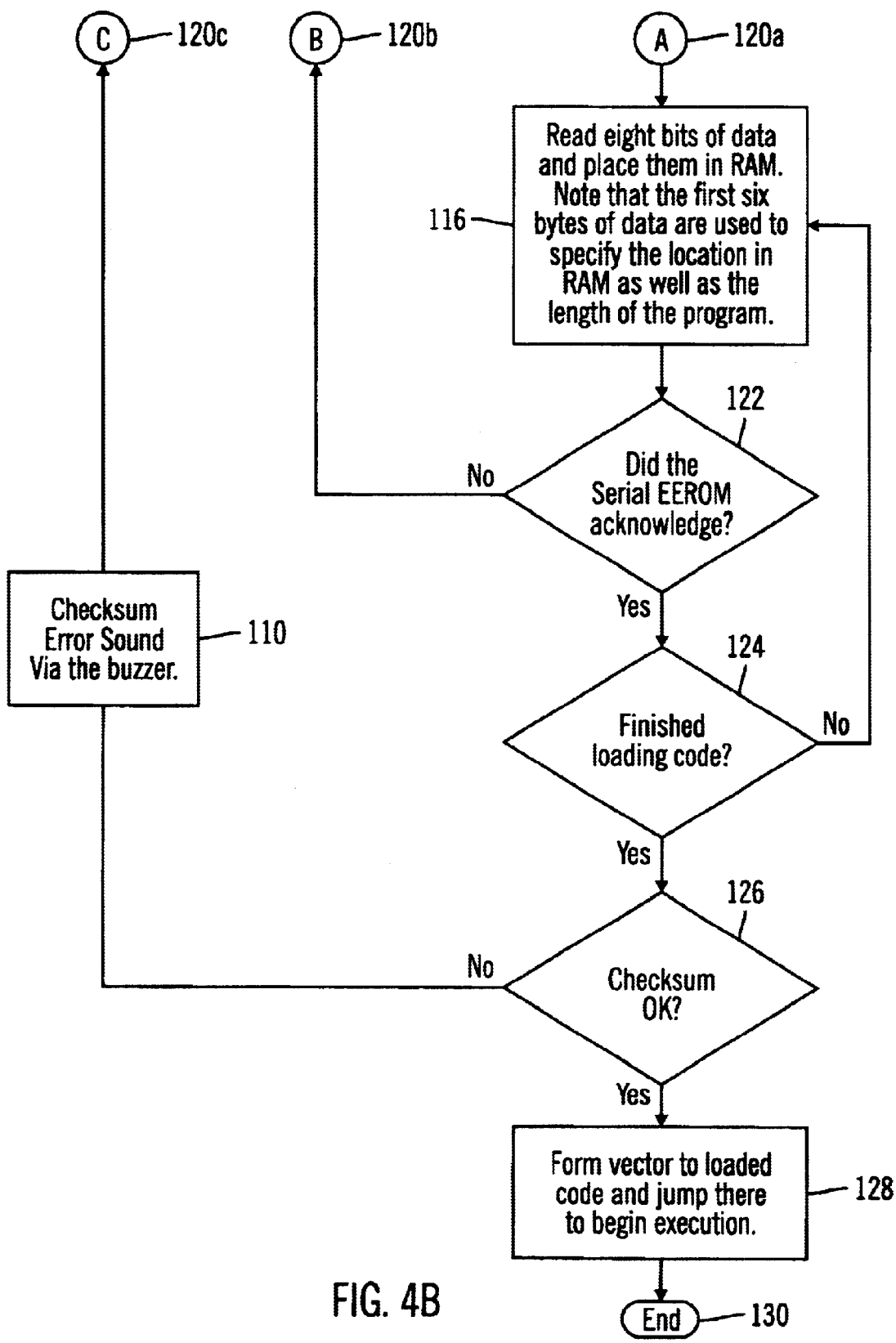

A flow chart depicting the process discussed above and used by the Processor IC Boot ROM is depicted in FIGS. 4a and 4b. Step 102 calls for the start of the CPU boot process. Step 104 indicates that the segment registers are initialized, power is shut off to unnecessary areas, and the watchdog is acknowledged. Step 106 indicates that a transaction is initiated with the SEEPROM. Step 108 inquires as to whether the SEEPROM acknowledged the transaction of 106. If "NO" the process moves to step 112. If "YES", the process moves forward to step 114. Step 112 calls for the sounding of an alarm via the buzzer located inside the implantable device or the external communication device and also calls for returning to step 106. Step 114 calls for a performing a read transaction from the SEEPROM. Step 116 inquires as to whether the SEEPROM acknowledged the transaction of 114. If "NO" the process moves to step 112. If "YES" the process moves forward to step 1018.

Reference 120A, 120B, and 120C are intended to show the flow connections between FIGS. 4a and 4b. Step 118 calls for the reading of eight bits of data from the SEEPROM and the placement of that data into RAM. The first four bytes of data are used to specify the location in RAM where the data is to be placed as well as the length of the program. Step 122 inquires as to whether the SEEPROM acknowledged the transaction of 118. If "NO" the process moves to step 112. If "YES", the process moves forward to step 124. Step 124 inquires as to whether or not the code has finished being loaded. If not, the process loops back to step 118. If "YES", the process moves forward to step 126. Step 126 inquires as to whether the check sum extracted from the SEEPROM matches the check sum for the remainder of the data extracted from the SEEPROM. If "YES", the process proceeds to step 128. If no, the proceeds to step 110. Step 110 calls for the sounding of a checksum error and then causes the process to begin again at step 104. Step 128 calls for the formation of a vector to the loaded code and a jump to that location so as to begin execution of the newly loaded code. Step 130 indicates the end of the process.

Upon execution the bootloader software (sometimes referred to as the second stage bootloader software or SSBS) takes control of the operations of the medical device including management of basic telemetry, management of inter-processor communications, copying of selected constants from permanent storage in the SEEPROM to RAM so that they may be accessed when needed, and control of alarm function. The second stage bootloader allows telemetry communications related to interrogating and linking communication devices with medical devices, loading new software, resetting the medical device, and performing read operations on the implantable device's memory (for diagnostic purposes).

Figure 5A:
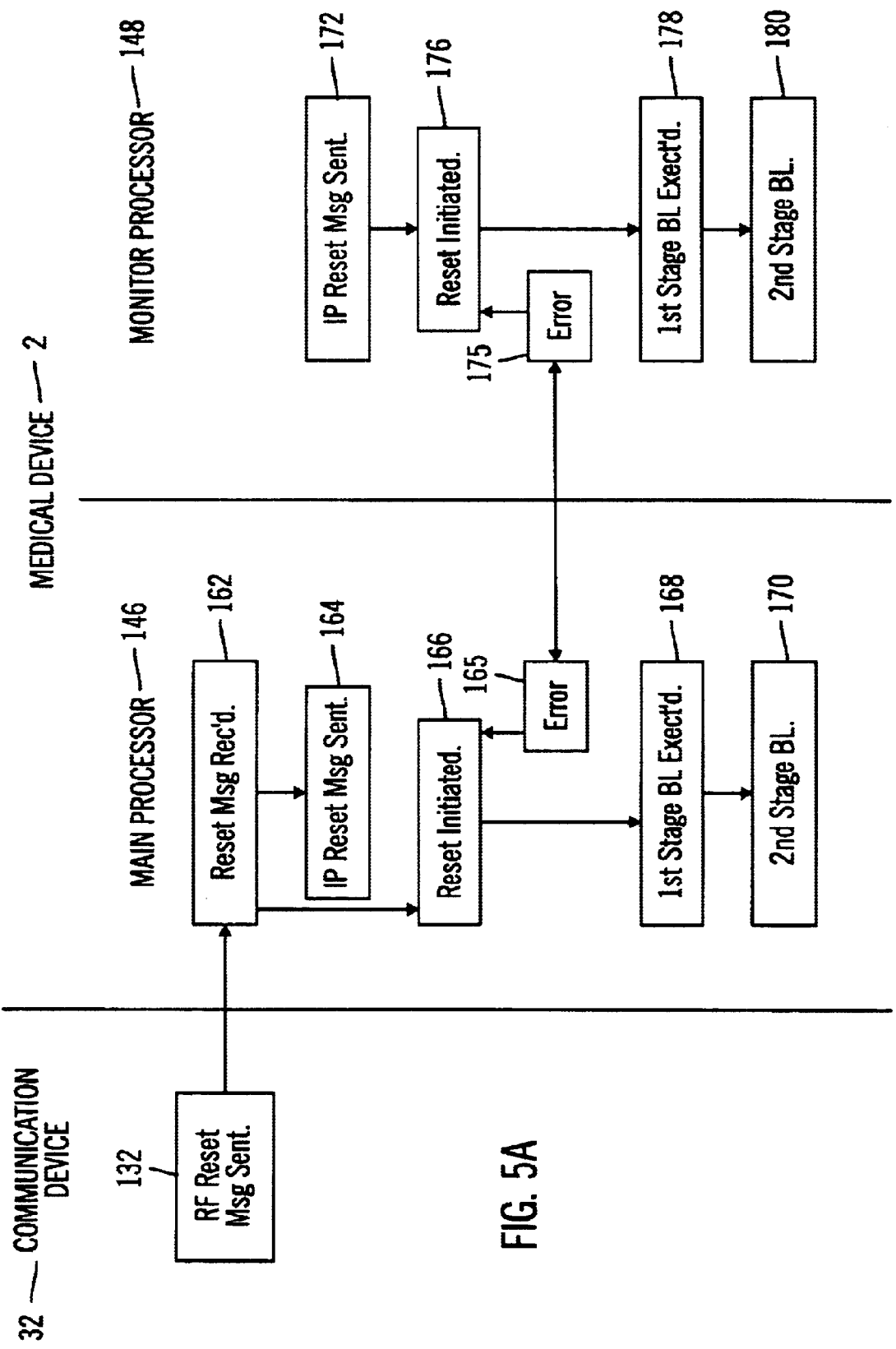
FIGS. 5a–5c depict a block diagram of overall application software download interactions that occur between the communication device and the two processors in the medical device when the medical device is operating under control of bootloader software.
Figure 5B:
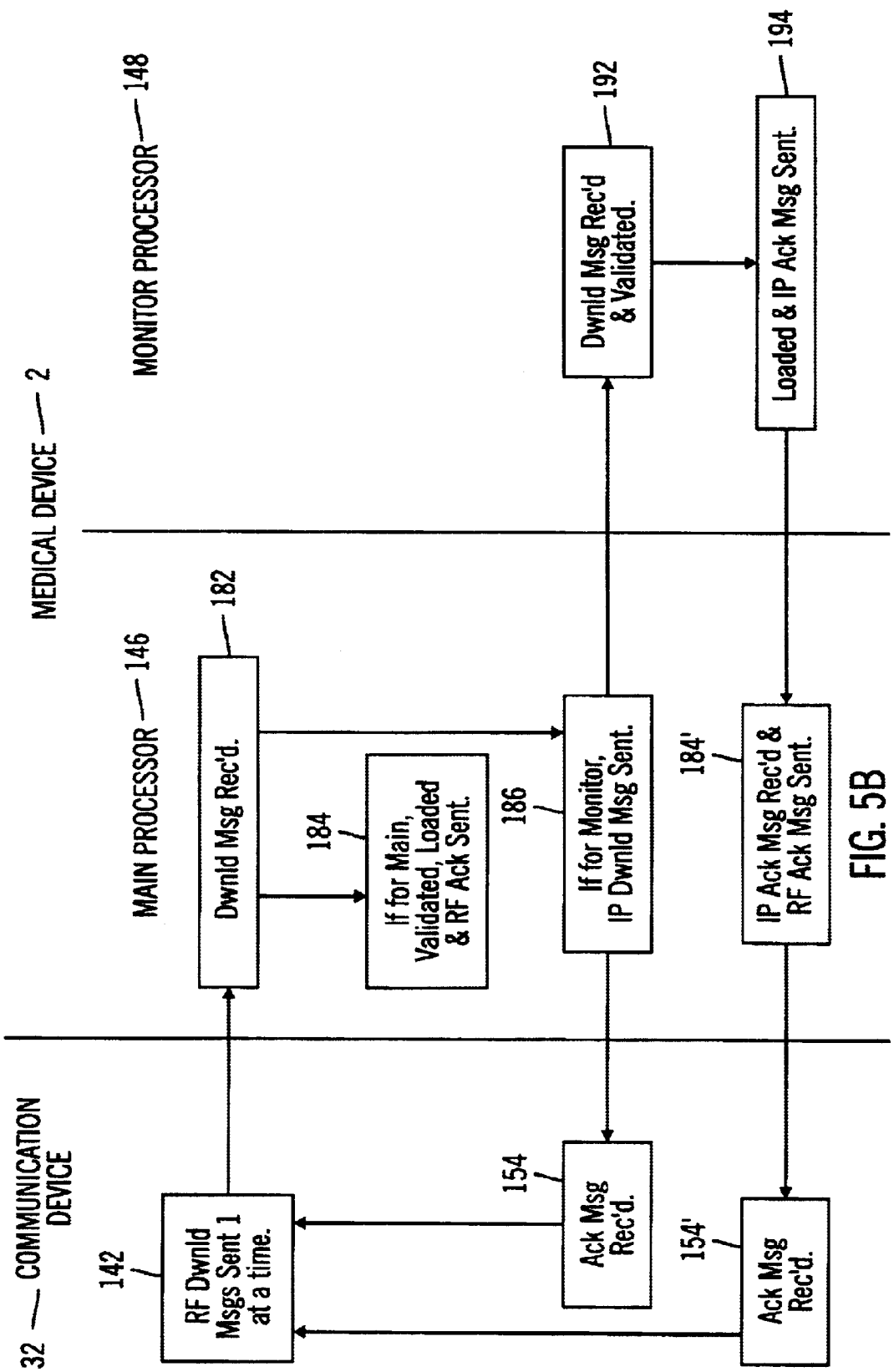
Figure 5C:
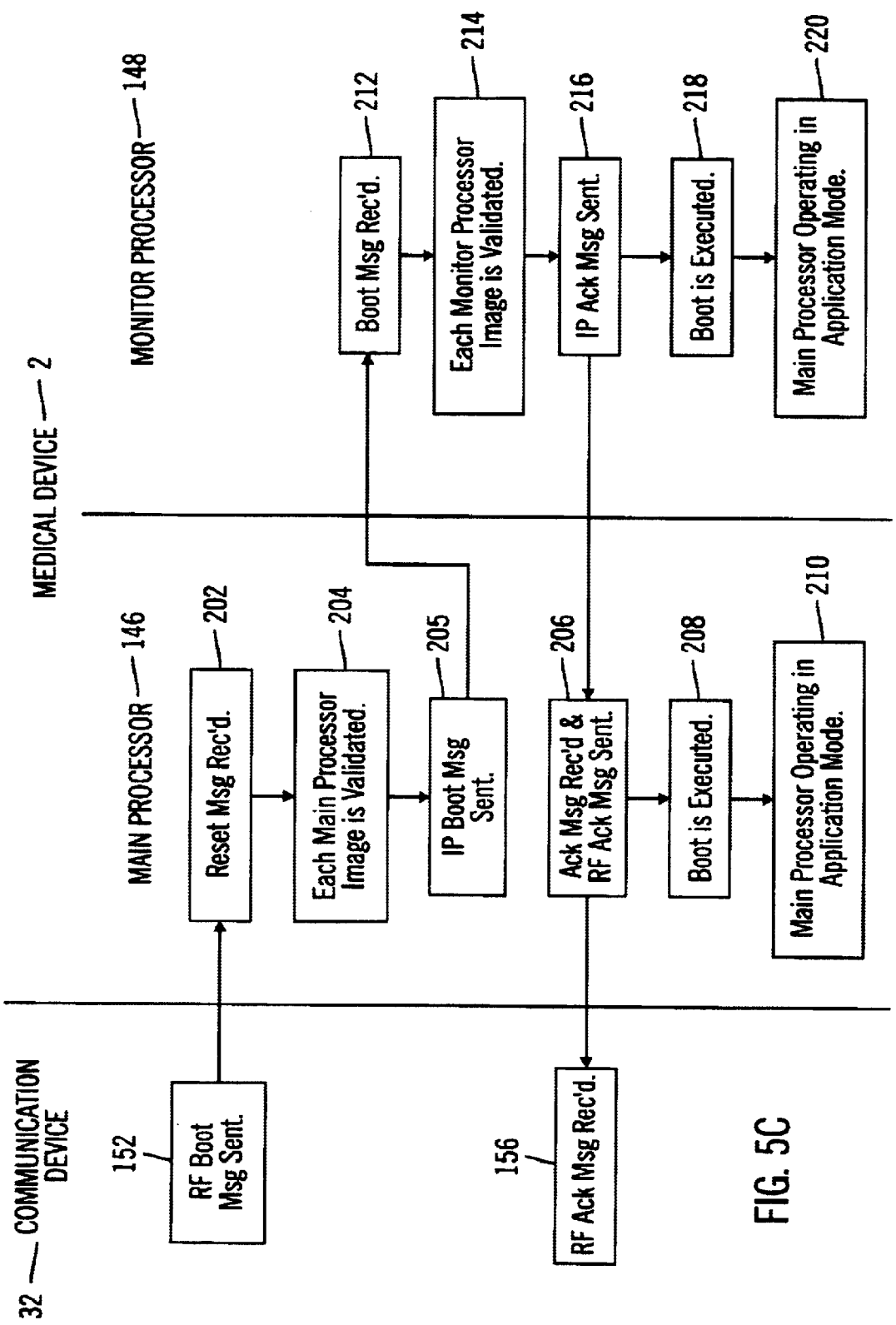

FIGS. 5a–5c provide a block diagrams of the primary second stage bootloader software operations and interactions relating to the downloading of new application software. Line 142 depicts the separation between the communication device 32 and the medical device 2 through which RF telemetry communications pass. Line 144 depicts the separation between the main processor and monitor processor through which inter-processor communications pass.

The communication device 32 issues three primary message types related to the downloading of new application software: (1) the reset message 132, (2) the download messages 142, and (3) the boot strap message 152. The download messages 142 actually consist of a repeated series of two messages: (1) the inbound load start message, and (2) typically multiple inbound load continue messages. The repetition of the download messages is controlled by the software operating in the communication device based on the number of software images that need to be downloaded and the number of messages that it will take to download each image.

The reset message is used to force the implantable medical device software to enter bootloader mode (i.e. reload the bootloader software) and to thereby exit application mode (stop execution of application software). This message may be sent out to prepare the implantable device to accept new software that can be supplied with inbound load start message, in conjunction with the inbound load continue messages, and then to restart the application software with a bootstrap message.

The inbound load start message provides the means to initiate the load of the implantable medical device with application software. The implantable device must be running in the bootloader mode for this command to have an effect. If the implantable device is in the bootloader mode, then the inbound load start message causes data in the message to be parsed and stored into the memory locations specified by the load data field of the message. Information contained in the message includes an indication as to software type (for the image to be downloaded), which processor the image is for, whether the image is executable (i.e. a software program as opposed to data), memory location where to place the image, a validation code for the overall image, and a validation code for the message itself. In the present context software "image" refers to the exact pattern of bits or bytes that make up a software program or at least a portion of it. This message does not contain any of the image itself that is to be downloaded. As the bootloader software expects to download a certain number of software images (e.g. 4 images—1 software code image for the monitor processor, 1 data image for the monitor processor, 1 software code image of the main processor, and 1 software data image for the main processor), the use of the inbound load start message is repeated after each image download until each expected image has been downloaded.

The inbound load continue message is the means to load the implantable medical device with application software. If the implantable device is in the bootloader mode, then the first inbound load continue message following an inbound load start message causes the image portion of the message to start loading into the memory location specified by the address information in the most recent inbound load start message. As the software is loaded, the address is updated by the implantable device such that subsequent inbound load continue messages have their data loaded in contiguous memory. As the external communication device is aware of the number of inbound load continue messages it will take to download the entire image, the sending of successive messages is repeated the required number of times after each message is confirmed to have been correctly received. The sending of the same message is repeated until a confirmation of its appropriate receipt is obtained or until the patient is informed of a problem so that further action may be taken. Once the data is loaded and the receipt of the message validated, the implantable device returns a response message. No response is returned if the validation of the message is not confirmed, in which case the implantable device simply awaits the resending of the message.

The bootstrap message is used to confirm that the validation code (e.g. CRC) for each downloaded software image is correct and then to cause both processors of the implantable device to transfer control from the bootloader software to the application software. If the calculated CRCs do not match the image CRCs transmitted with their respective inbound start download messages, an error message is sent to indicate that there was a failure, and the system control remains with the bootloader software (i.e. the system remains in bootloader mode). In some embodiments, this error may give rise to a retransmission of all software images or only those that could not be validated. If the implantable device is operating under control of the application software when the bootloader message is received, the message is acknowledged without re-executing the software that is already controlling operations. In embodiments where the reset operation and the reloading of the bootloader software doesn't damage the application software images previously loaded in the medical device, it may be possible to simply restart the application software, after image integrity verification, using this command without reloading the application software first.

As indicated in FIG. 5a, the reset message 132 is sent out by the communication device 32 so that it is received by the telemetry system connected to the main processor 146 of medical device 2, as indicated by block 162. The main processor, under control of the second stage bootloader software generates an inter-processor (IP) reset message 164 that is sent to and received by the monitor processor, as indicated by block 172. Once the reset message is passed on to the monitor processor, both processors are reset as indicated by blocks 166 and 176. The resetting of the processors occurs by each processor causing its watchdog to be tripped. The resetting causes the first stage bootloader in both processors to execute as indicated by blocks 168 and 178 which is automatically followed by the execution of the second stage bootloader software as indicated by blocks 170 and 180. In the present embodiment, the communication device receives no telemetry feedback concerning the medical device's receipt of the reset message.

As indicated by blocks 165 and 175, reset of a processor can occur by the processor itself detecting an error. An error 165 of significant magnitude detected by main processor may cause the initiation of a main processor reset as depicted by arrow running from block 165 to 166. Similarly an error 175 of significant magnitude detected by the monitor processor may cause a monitor processor reset as depicted by the arrow running from block 175 to 176. A double-headed arrow connects blocks 165 and 175. This double arrow indicates that an error condition in one processor that results in resetting that processor will also trigger an error condition in the other processor that will cause it to reset. When one of the processors is reset as a result of it detecting an error, the other processor will sooner or later unless tripped by a different error first, detect an error related to an inter-processor communication failure that will cause it to reset as well.

When input is received from the user (e.g. patient, physician, nurse, or technician), as depicted in FIG. 5b the communication device sends out the download messages 142 one at a time by RF telemetry. The download messages are actually a series of messages that include an inbound download start message and potentially multiple inbound load continue messages for each software image to be downloaded. For example, in one embodiment the series of messages may be repeated four times as four images are to be downloaded. As indicated by block 182, each download message is received by the main processor. If the received message is for the main processor, the main processor validates the integrity of the message, loads the software image to a desired location in memory and sends an RF acknowledge message, block 184, to the communication device. The communication device receives the acknowledgment as depicted in block 154 and the process loops back into block 142 for downloading of any further messages.

For messages that pertain to the monitor processor, the main processor prepares an IP download message as indicated in block 186. The IP download message is then received and validated by the monitor processor as indicated by block 192. In an alternative embodiment validation of monitor processor messages may be performed by the main processor prior to passing them on to the monitor processor. Next, the monitor processor loads the software image into a desired location in memory and then prepares and sends an IP acknowledgment message as indicated in block 194. The main processor receives the IP acknowledgement message and prepares an RF acknowledgment message as indicated in block 184'. The RF acknowledgment message is then sent to and received by the communication device as indicated by block 154'. After receipt of the RF acknowledgment message the process loops back up to block 142 for downloading of any further messages.

After all the software images have been downloaded, as depicted in FIG. 5c an RF bootstrap message 152 may be issued by the communication device (e.g. based on user input). This message is received by the main processor as indicated in block 202. After reception, the main processor confirms the integrity of previously downloaded software images as indicated by block 204. The main processor then prepares an IP bootstrap message as indicated by block 205. The IP bootstrap message is sent to and received by the monitor processor as indicated by block 212. After receipt of the IP message, the monitor processor confirms the integrity of the previously downloaded software images as indicated in block 214 after which an IP acknowledgment message 216 is prepared and sent to the main processor. The main processor receives the IP acknowledgement message as indicated by block 206 and then prepares and transmits an RF acknowledgment message to the communication device. The communication device receives the RF message as indicated by block 156.

After each of the monitor and main processors send their acknowledgments 216 and 206 respectively, they each independently turn over control to their respective application programs by executing jump commands to the beginnings of their respective executable application software images.

The telemetry communications allowed by the software occur in the form of messages (i.e. communication signals or packets) that are passed between the two devices. These messages have a multi-part format: (1) preamble, (2) frame sync, (3) telemetry identifier, and (4) data.

In the present embodiment, the telemetry identifier (i.e. telemetry ID) is a unique multi-byte (e.g. 3 byte) value that is used to ensure that most messages that are received are only acted upon when they are specifically intended for the that particular receiver. Some messages may be sent with a universal ID value that can be acted upon by multiple devices. Furthermore, the present embodiment requires an exchange of information between the two devices prior to the medical device being able to accept commands from the communication device that impact the medical functionality of the medical device. More particularly a monogamous communication link is established between the two devices by the exchange of information. In the most preferred embodiment, the telemetry ID of transmitter is sent implicitly within each message and the receiver must know the transmitters ID in order to decode or verify the accuracy of the message. In the preferred message format, the telemetry ID is followed by an op-code (e.g. 1 byte in length) that indicates the message type.

Each op-code, based on its nature, is followed by data in a defined number of bytes. The specific op-code itself may dictate the number of bytes that follow or alternatively the specific op-code may dictate that the number of bytes to follow may be extracted from the first byte or several bytes of information that follow it. Based on the op-code and potentially one or more bytes following it, the receiver knows exactly how many more bytes of data to listen for.

The data portion of the message may be up to 512 bytes and ends with a one or 2-byte validation or error checking code (its type is dictated by the op-code included with the message). The preferred error checking code of this embodiment is in the form of a cyclic redundancy code (CRC). In other embodiments, the CRC may be replaced with another error checking code and/or it may be placed in a different part of the message. It is preferred that the CRC be generally computed using the telemetry ID of the message originator (i.e. the telemetry ID of the transmitter). This serves as a form of security. If a message with this type of CRC is received by a medical device, the medical device must have advanced knowledge of the telemetry ID of the transmitting communication device or the medical device will reject the message because of a CRC error. Similarly the communication device preferably rejects messages coming from other medical devices than the specific one that it is linked to so that no confusion can occur by the inadvertent receipt of a command acknowledgement or alarm signal.

A CRC to be included with a message, in the present embodiment, is calculated based on the successive bytes forming the message and possibly upon the identity of the transmitter as well. When the CRC is computed using the telemetry ID of the message originator, the first three bytes used in the calculation are the telemetry ID of the originator. The CRC calculation then uses the three bytes of the telemetry ID of the intended receiver, one byte of op-code, and then the remaining bytes of data in the message (with the exception of the CRC itself that is being calculated).

Further details about CRC generation may be found in (1) above referenced concurrently filed US Patent Application (Docket No. USP-1079-A), (2) the "CCITT Red Book", Volume VIII, published by International Telecommunications Union, Geneva, 1986, Recommendation V.41, "Code-independent Error Control System", and (3) "C Programmer's Guide to Serial Communications", 2nd Edition, by Joe Campbell, published by SAMS Publishing, Indianapolis, Ind., ISBN 0-672-30286-1. In particular chapter 3 of this latter book deals with errors and error detection including CRCs, while chapter 23 deals with calculation of CRCs. These books are hereby incorporated by reference herein as if set forth in full.

Additional teachings concerning the telemetry system and protocol used in communicating messages is provided in previously referenced United States Patent Application Nos. (Docket Nos. USP-1076-A, USP-1077-A, and USP-1079-A).

Software may be downloaded from the external communication device to the implantable device. The downloading of software may include not only the downloading of executable software but also the downloading of data structures that may be used by the executable software. In the present embodiment, The downloading of software may be only occur when the implantable medical device is in a bootloader operation mode. As noted above, the bootloader operation mode is an intermediate operation state where various communication activities can occur but where medical functionality of the implantable device is inactivated or strictly limited to a default mode of simplified operation. New software may be of the application type or of the bootloader type. In the present embodiment, new application software is always loaded for and to both the main and monitor processors at the same type. Replacement bootloader software may be loaded for either processor individually. Also as noted above, application software is the software that controls normal medical operation of the device along with telemetry operations when it is in control of the device. Bootloader software is the software that initially controls of the device immediately after start up and resetting. As such, in more preferred embodiments, the software controlling the implantable medical device will allow certain communication operations to occur and will also allow either the downloading of new software or the normal medical operations of the device but not both simultaneously. In alternative embodiments, device operation may be modified so that application software may be loaded to either processor individually or so that downloading of software need not be limited to periods when the bootloader software is being executed.

The bootloader mode may be initiated in the implantable device by sending it a reset message from the external communication device. Downloading may be initiated by using a inbound load start message that includes an overall validation code (e.g. CRC) for the program that is to be downloaded (i.e. software image) along with its normal message validation code (e.g. CRC) that is used to confirm that the start download message itself was properly received. The software may be downloaded from a non-volatile memory module (e.g. a SEEPROM) in the external communication device, or from a second external device, that holds implantable device software. Downloads then occur using one or more inbound load continue messages each having data portions (excluding op-code and validation code). In the present embodiment, when loading application software, the inbound load start and inbound load continue messages are sent in series four times one for each of two images for the main processor (one executable and one data) and for each of two images for the monitor processor (one executable and one data). Each message that is sent carries its own validation code, that must be acknowledged as valid if the message is to be accepted and acknowledged before additional messages are sent. Each image sent is identified as being of the data or executable type and as being intended for the main processor of the monitor processor. If intended for the main processor, the main processor verifies the validity of the message and stores it to a selected location in memory. If intended for the monitor processor, the main processor receives the message over the telemetry system, verifies the validity of the message and passes it along to the monitor processor to storage at a selected location in its memory. In alternative embodiments, downloads may occur from a second external device either directly to the implantable device or via the external communication device.

Once all program images for application software have been downloaded, the new software is executed by transmitting a bootstrap message. A final validation code (e.g. CRC) for each program image that is supplied by the external communication device is compared to a validation code (e.g. CRC) that is derived for each program image directly from the data that was received and stored. For each calculated program image validation code that doesn't match the transferred validation code, an error message is sent to the external communication device and that program image is completely reloaded. In any event, until all programs are confirmed to have been appropriately received, the implantable device remains in bootloader mode. Once each calculated validation code and each transmitted validation code match for each program image, the monitor and main processors turn over control to their respective newly downloaded programs.

If the downloaded programs are replacement bootloader programs, once the validation codes (e.g. CRCs) are confirmed, the program images are copied over into their permanent positions within a non-volatile memory module and the device is reset so that upon reboot, the new bootloader code is executed. After booting with the new bootloader programs, new application software may be downloaded using the above noted process.

In alternative embodiments, after the external communication device has sent message containing the final portion for each image, the overall CRC for that entire image may be calculated and compared to the code that was transmitted from communication device. If the two codes appropriately compare (e.g. match), the download of that program is considered valid and then the next program image may be downloaded using the the same procedure. If the overall CRCs do not match the entire program is resent. Once all programs have been downloaded, the new code is executed by transmitting the bootstrap message from the external communication device or other external device.

The transmitted CRCs, the initially calculated CRCs (once confirmed to be correct), a CRC based on an initially configured software image (if not completely configured at the time of transfer), or other validation code may be retained by the implantable device and used to periodically confirm that the stored software images retain their integrity (i.e. that the software has not been corrupted).

In alternative embodiments, instead of an overall CRC being sent for each program, two overall CRCs may be sent where one is for the monitor processor IC images that were transmitted while the other is for the main processor IC images that were transmitted. In still other embodiments, a single overall CRC may be transmitted for all programs regardless of the processor IC on which they will be used.

Figure 6A:
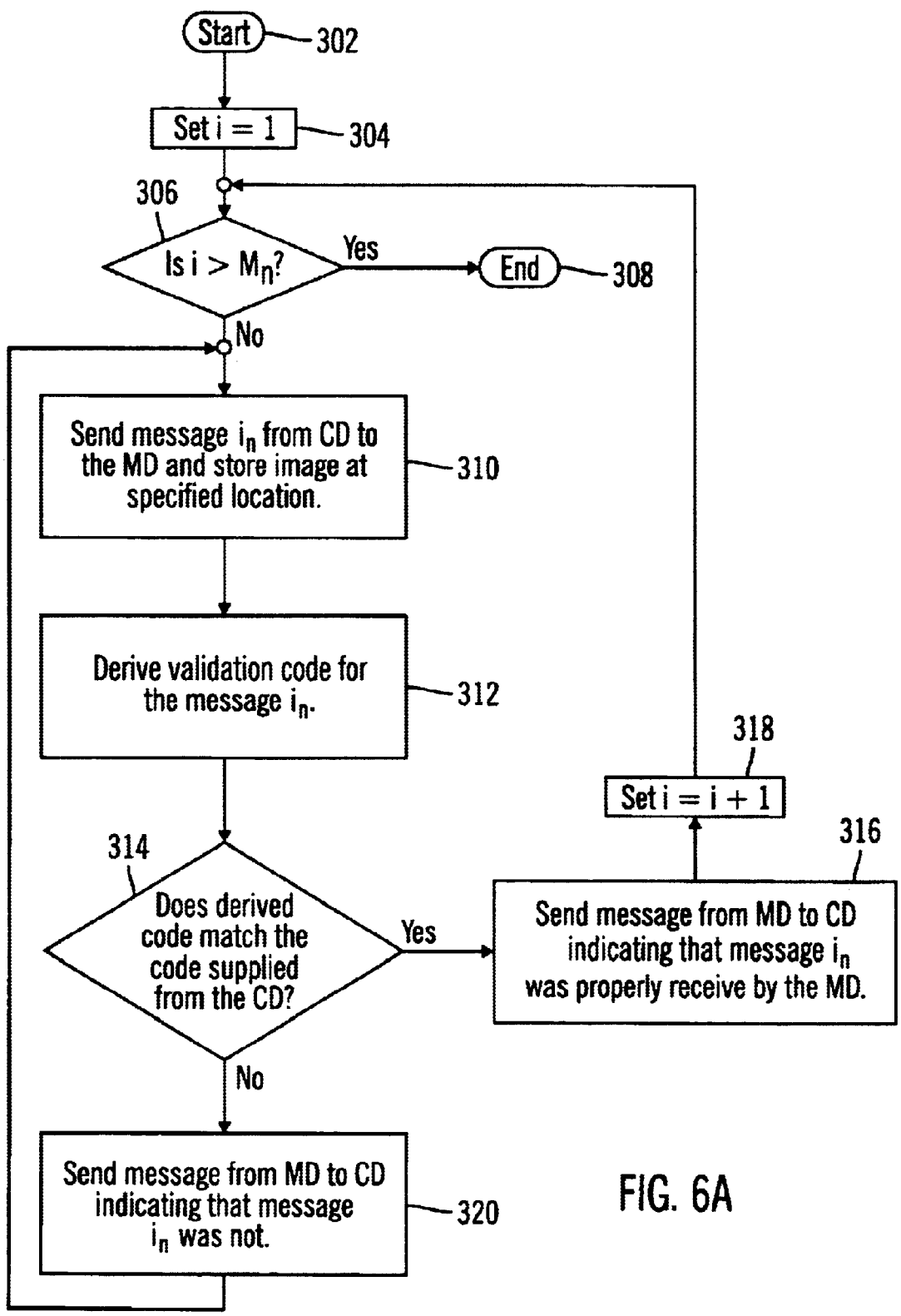
Figure 6B:
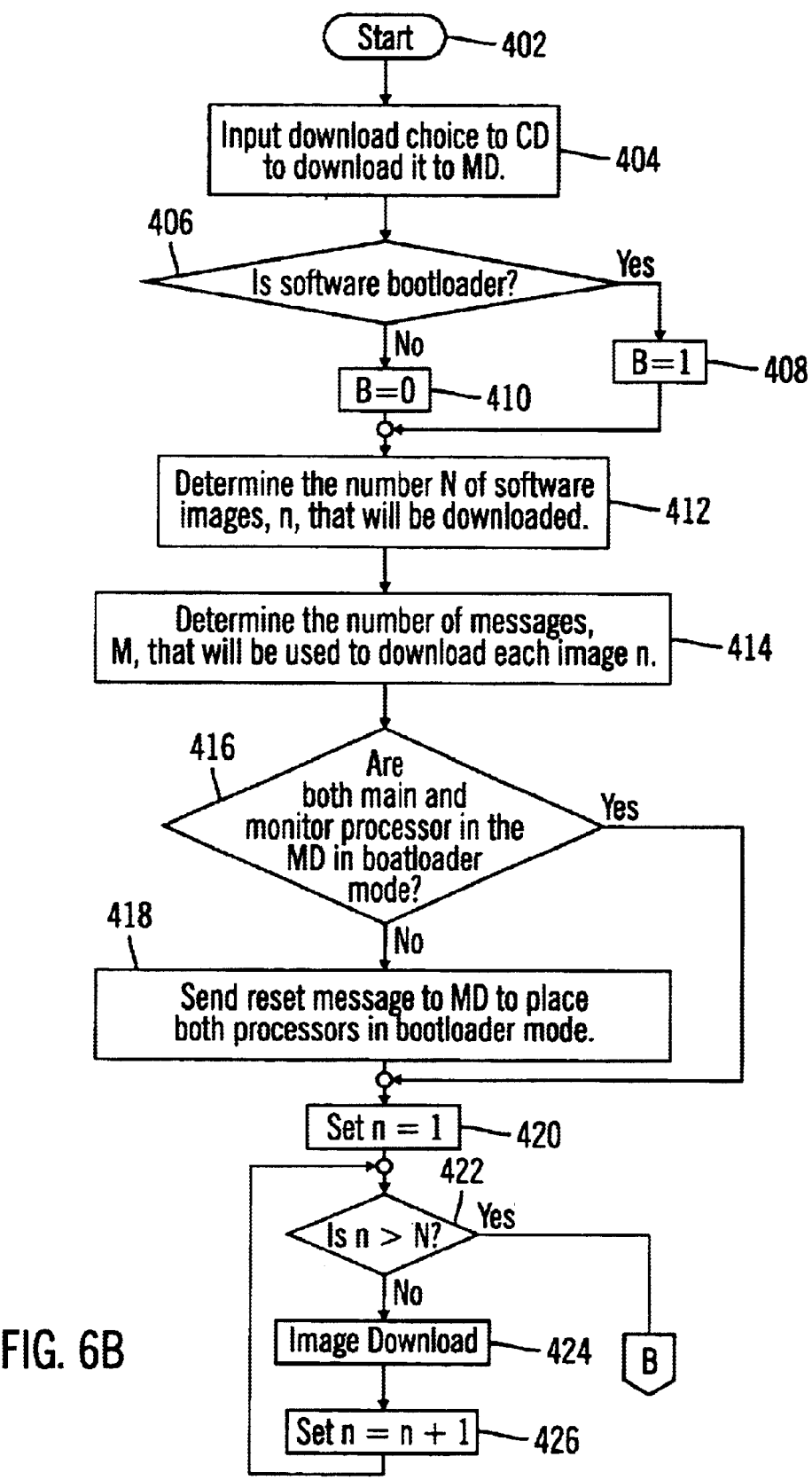
FIGS. 6b–6c depict a flow chart of a preferred implementation of downloading replacement software from the communication device to the medical device.
Figure 6C:
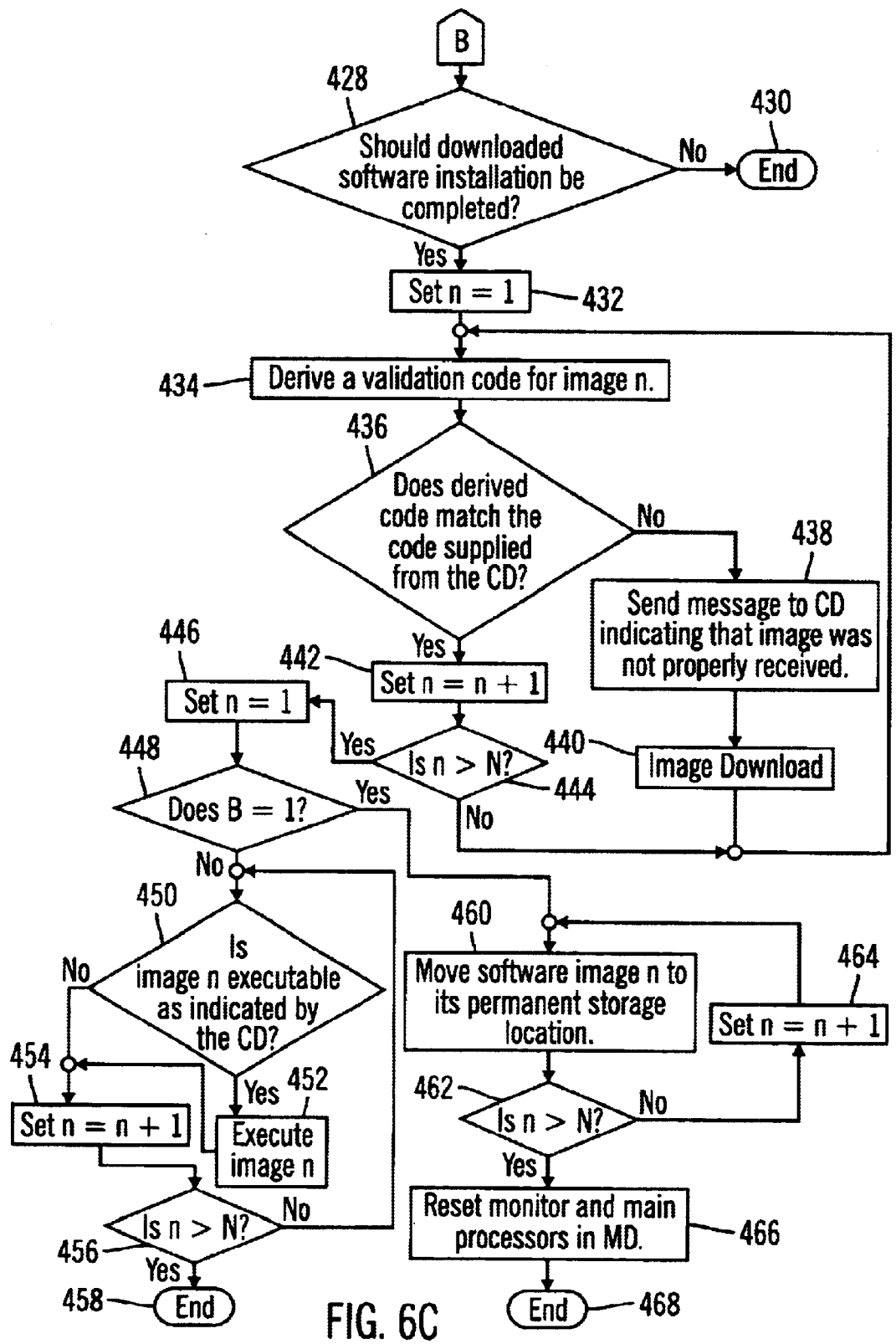

FIGS. 6a–6c provide a flowchart that details how software of either the application type or bootloader type may be downloaded in a preferred embodiment of the invention. FIG. 6a depicts a process flow that may be used in downloading a single software image whose size requires that potentially more than one message be used to complete the download process. In particular the process is entered at step 302. At step 304 a first control variable "i" is set to a value of 1. This variable is used in the process to indicate the portion of the software image that is currently being processed.

Step 306 inquires as to whether control variable "i" is greater than a parameter $M_n$. If it is greater, the process moves to step 308 and ends. If it is not greater, the process moves forward to step 310. In the present embodiment, the parameter $M_n$ is the total number of distinct messages that are required to download image "n". Step 310 calls for the communication device to send message $i_n$ (i.e. the "i"th message of image "n") and to store the image sent with that message at a specified location in memory. In this embodiment, no distinction is made with regard to whether the image is being stored in association with a first (e.g. main) or second (e.g. monitor) processor. It will be understood by those of skill in the art that such an extension to the process could be made if and when necessary. Next, step 312 indicates that a validation code for the message is derived.

Next, step 314 inquires as to whether the derived validation code matches a validation code supplied from the communication device. If the codes compare appropriately (e.g. match), the process moves forward to step 316. Step 316 calls for an acknowledgment message to be sent from the medical device to the communication device indicating that the message was properly received. The process then continues on to step 318 where the control variable "i" is incremented to "i+1", whereafter the process loops back to step 306. This continuation of the process preferably occurs within the communication device as the acknowledgment just received by it, indicated that the medical device is ready for the next piece of the image.

Turning back to step 314, if the codes did not compare properly, the process moves to step 320. Step 320 calls for a message to be sent to the communication device indicating that download of the "$i_n$"th message failed whereafter the process loops make to step 306 without incrementing the value of "i" so that another attempt is made to download the same message and thus same portion of the software image. In any event, once the process has successfully looped through and completed downloads of messages $1_n$, $2_n$, $3_n$, ... $M_n$. the process is completed and ends at step 308.

Though not indicated in this flowchart, it may be desirable to set a limit to the number of retries that will be automatically attempted without informing the user of the failures. In one alternative, each failure may require user acknowledgment while in others, for example, 3–10 may be automatically tried before informing the user of the failures. When the automatic number of attempts have been made, the message sent in step 320 may then require patient acknowledgment before any subsequent download is attempted. When informed of the failure(s) the communication device may request that the user relatively reposition the communication device and the medical device or move to a different location prior to proceeding with further download attempts.

FIGS. 6b and 6c combine to present a single flowchart that depicts a complete process flow routine that might be used in downloading and executing all necessary software images of either the application or bootloader type. The process starts at step 402. It then proceeds to step 404 where the type of software to download is selected. Next at step 406 the process inquires as to whether the selected software is of the bootloader type. If "yes", step 408 sets a variable B to a value of one. If "no", step 410 sets the variable B to a value of zero. Variable B will be used near the end of the process to determine how execution of the newly loaded software should occur. If only two downloading options exist, step 404 may be largely redundant to step 406. As the value given to variable B in steps 408 or 410 will only be used near the end of the process, in an alternative embodiment, these operations may be delayed to a later point in the process. Whether passing through step 408 or 410 the next step is 412. Step 412 calls for a determination as to the total number "N" of software images "n" that will be downloaded. In a presently preferred embodiment discussed above, the total number "N" is four. Next, step 414 calls for a determination as to the number of messages "$M_n$" that will be used in downloading each image "n".

The process then continues with step 416 which inquires as to whether both the MD main and MD monitor processors are operating in bootloader mode. If "yes", the process jumps to step 420. If "no", the process passes through step 418 prior to moving to step 420. Step 418 calls for the communication device to send a reset command to the medical device so as to ensure that both processors are placed in bootloader mode. At step 420, the image number variable "n" is set equal to one.

At step 422, an inquiry is made as to whether "n" is greater than "N". If "yes", the process moves forward to step 428. If "no", the process moves forward to step 424. Step 424 calls for downloading of the entire software image "n". Step 424 may be executed according to the process set forth in FIG. 6a after which the process can continue on to step 426 where "n" is incremented to "n+1". After incrementing "n", the process loops back to step 422. The process will then either loop back through steps 424 and 426 to download the remaining images for each incremented value of "n" or if "n" already exceeds "N" the process will proceed on to step 428. When the process is ready to proceed on to step 428, all software download message have been received and individually verified. If the answer to the inquiry of step 428 is "no", the process terminates at step 430. If the answer is "yes", the process moves forward to step 432 where the image number variable "n" is again set to a value of one. At step 434, a validation code for the entire image "n" is derived from the downloaded data for the entire image.

Next step 436 inquires as to whether the derived validation code compares appropriately to the validation code supplied from the communication device. If "no", the process proceeds to step 438 which calls for the sending of a message from the medical device to the communication device indicating that image "n" was not properly received, after which the process proceeds to step 440. Step 440 calls for the downloading (i.e. a repeated downloading) of software image "n". This downloading process may be performed according to the process depicted in FIG. 6a. After again obtaining a download of the image "n" the process loops back to step 434 for another pass through the validation steps. Turning back to step 436, if the answer was "yes", the process moves forward to step 442 where image number variable "n" is incremented to "n+1" and then on to step 444.

Step 444 inquires as to whether variable "n" has exceeded the total number of images that have been downloaded, i.e. parameter "N". If not, the process loops back to step 434 so that the validation process may be repeated for the next software image. If the answer to the inquiry of step 444 is "yes", the process moves forward to step 446 where image number variable "n" is again set to a value of one after which the process moves on to step 448.

Step 448 inquires as to whether the bootloader variable is set to one. If "yes", the software is bootloader software or if "no" the software is application software. If "yes", the process moves forward to step 460 which calls for the moving of the software image to its permanent location (i.e. into non-volatile memory such as a SEEPROM or the like).

Next, the process moves to step 462 where an inquiry is made as to whether "n" is greater than "N". If "no", the process loops back to step 460 after first incrementing "n" to "n+1", in step 464, so that additional software images may be moved to permanent storage. If the answer to the inquiry of step 462 was "yes" then the process moves forward to step 466 where the medical device forces its two processors to reset so that the device may reboot under the control of the newly loaded second stage bootloader software. After which the process ends at step 468.

Turning back to step 468, if the answer to the bootloader inquiry was "no" then the process proceeds to step 450. Step 450 inquires as to whether software image "n" is executable as indicated by the communication device, if "yes" the image is executed and the then the process proceeds to step 454. If the answer were "no" the process proceeds to step 454 without attempting to execute the software. In step 454, variable "n" is incremented to "n+1", then the process moves to step 456.

In step 456 the inquiry is made as to whether "n" is greater than "N". If "no" the process loops back to step 450 thereby allowing other executable software images to be executed. If "yes", the process proceeds to step 458 and terminates.

The process illustrated in FIGS. 6a–6c may be generalized to four primary steps: (1) set up the system for the download—steps 402 to 418, (2) download each message for each image and validate the individual messages to confirm proper reception—steps 120 to 126, (3) validate each image as a whole—steps 132 to 144, and (4) turn over control to the newly downloaded software—steps 148 to 168.

In the present embodiment, inactivation of previously installed application software is ensured upon boot up as the bootloader program clears the memory (e.g. writing zero's to each bit) where the validation codes are located that are used in ensuring the integrity of the software program images. As such, if execution of application code loaded prior to rebooting, were attempted by use of a boot command, the attempt would fail due to a validation code failure (e.g. CRC failure). In other embodiments this safety feature could be relaxed to allow execution of previously loaded application software to occur at least under certain circumstances. For example, if resetting of both processor in the implant occurred by use of the reset command, as opposed to by error detection, then software re-execution could be enabled by a boot command that first writes validation codes stored in another part of memory to the location where they are used for validation purposes.

In different embodiments, various modifications to the above presented embodiments and alternatives are possible. For example, though two processors are preferred in controlling the medical device as a safety enhancement, the medical device need not operate with two independent processors, particularly if other components are added to monitor critical processor activities. In other alternatives, the validation of generalized step 2 of FIGS. 6a–6c may be dropped if the validation of generalized step 3 is considered adequate, or vice-a-versa.

A further enhancement to the process of FIGS. 6a–6c might involve ensuring that any criticality in the execution order, associated with step 452, for the various software images be accounted for by assigning image numbers "n" in an appropriate order to specific software images. Alternatively, the process may be modified so that all executables are executed simultaneously. As another example, step 160 may be deleted if the software is stored to its permanent location upon initial download. In an additional example, in steps 416 and 436 various relationships beside strict bit-by-bit matching of the codes may be used in verifying the integrity of the received messages or images.

In an alternative embodiment, a modification to the flow routine and/or system operation could be made so that bootloader and application software could be downloaded simultaneously. In particular, if there is no conflict between the temporary or permanent loading locations of the two types of software, either when performing the initial download or upon boot up after reset, then both types of code could be downloaded in the same process. The downloading may be followed by validation of all images, followed by reboot, and then followed by execution of the already downloaded application software. Alternatively, instead of rebooting, the bootloader software may be moved to its permanent location and execution of the application software may occur such that the first use of the new bootloader software would occur at some point in the future after an intentional or error based reset operation.

The process of booting the Implantable Device, from reset to the running of application code, may be looked at as a multistage process. These multiple stages provide for safe operation of the system, upgradability, and significant in situ diagnostic capabilities.

The various features of the present embodiment may be used in providing a more robust, more effective, more reliable, extended, and/or safer operation of an implantable medical device and more generically for an ambulatory medical device.

While the above teachings have been primarily concerned with an implantable infusion pump that dispenses insulin, the software control and download capabilities as described above may be used in various other ambulatory devices: (1) implantable pacemakers, (2) defibrillators, (3) other implantable tissue stimulators, (4) implantable physiologic sensors such as electrochemical oxygen sensors, peroxide sensors, or enzymatic sensors such as glucose sensors, (5) externally carried infusion pumps, (6) implantable infusion pumps that use various pumping mechanisms or simply use excess pressure and controlled flow elements to infuse various medications and drugs such as analgesics, drugs for treating AIDS, drugs for treating psychological disorders, and the like.

In these various alternatives, the physical, electronic, and programmed features of the communication device and implantable device may have different components and features than presented above for the implantable pump system so that their desired medical functionality and safety requirements are achieved and such that appropriate control and feedback is provided between the medical device and its communication device.

In other alternative embodiments the medical device may include two medical devices such as an implantable pump and an implantable sensor. The pump may dispense a drug whose physiological impact on the body (e.g. analgesic impact) is ascertained by the sensor or alternatively the sensor may supply a physiological reading that indicates a need for infusion of the drug. The pump may operate in a closed loop manner with the sensor or it may operate in an open loop manner where the patient is required to interpret sensor output information and make decisions concerning appropriate amounts that the infusion pump should be made to dispense. For example, in the case of a diabetic patient, the drug may be insulin and the sensor may detect glucose level.

In embodiments that include two implanted medical devices the two medical devices may be implanted adjacent one another or at an extended distance from one another. If not placed in physical contact with one another, a lead may be used to provide power conduction from one device to the other and also be used to conduct communication signals between the devices. Alternatively, each device may include at least one telemetry system that allows direct communication or allows indirect communication to occur via the external communication device or other external device. Each device may be supplied with its own power supply. Depending on the communication requirements each device may use two way communication (i.e. both outbound and inbound communication) or allow only one way communication (i.e. outbound communication or possibly inbound communication). Various telemetry systems may be used. For example, telemetry systems may be of the analog type, digital type, or mixed. They may be RF based, IR based, optically based, inductively based, acoustically based, have some other basis that allows communication signals to be transmitted safely through the body and picked up by a receiver. Replacement software may be supplied to both medical devices directly from the external device or be supplied to only a first of the medical devices from the communication device and then to the second of the medical devices from the first medical device.

In other alternatives, both the medical device and the communication device may be external devices (e.g. an external pump and an external RF telemetry based communication device). In still further alternatives, a first type of medical device may be implanted (e.g. an infusion pump or a sensor) while a second medical device may be external (e.g. the opposite of a sensor or an infusion pump). Where at least one of the medical devices is external, it may also function as the communication device for the other medical device in which case it may possess a display for providing information to the patient and a keypad for allowing entry of commands for issuance to the implantable device as well as for direct use by itself. Even if at least one of the medical devices is external, it may be inconvenient to access that device when information is needed or commands must be given, as such an external, non-medical communication device may be supplied that has information output (e.g. display) capabilities and input (e.g. keypad) capabilities. If a separate communication device is provided, the external medical device may or may not have display and input capabilities.

The download capabilities presented herein may be used with various forms of distant communication other than RF (e.g. between the implantable device and other external devices or between the external communication device and other external devices) via various electromagnetic links like IR, optical links, longer or shorter wavelength RF, audio links, ultrasonic links, and the like.

In other embodiments two independent processors may be used that operate from a single timing chain. In these alternatives, it is preferable that at least one of the timing signals (e.g. one of the lower frequency timers) be monitored by an independently timed watchdog circuit to reduce the risk of timing problems going undetected.

In still additional embodiments, an implantable glucose sensor may be used in conjunction with an implantable insulin pump to provide feedback to the patient or physician on the effectiveness of the insulin delivery system. The patient could use the feedback to assist in making insulin delivery decisions in an open loop manner. Alternatively, the operation of the pump could be tied to the sensor output in a more or less closed loop manner to give a more automated character to system operation. Insulin may be infused without any user intervention, without pre-delivery information, and even without direct post delivery feedback. In a less automated closed loop system, drug infusion recommendations could be derived by the system and presented to the user before delivery or the system could require user acknowledgment prior to proceeding with delivery for amounts or rates exceed a predefined limit. The implantable sensor may have its own power supply or may receive power from the control circuitry provided within the pump housing through a physical lead that connects them. Power may be supplied through one or more independent leads or alternatively may be transferred over one or more data lines through the communication signals themselves. Communication may be exchanged in various ways including, for example, via galvanic leads, RF telemetry, fiber optics, and the like, and may be of digital, analog, or combined form. The sensor system may include a plurality of sensor elements which might allow continued glucose data to be supplied even though some portion of the sensors stop operating, lose calibration or produce questionable readings. The most preferred sensors would include electronic processing capability in the form of an integrated circuit mounted in or forming a part of a housing for the sensor. This configuration has the advantage of allowing digital communications between the physical sensor and any separated electronic control module.

Further teachings concerning implantable sensors and implantable sensor systems are found in a number of patents issued to D. A. Gough, including (1) U.S. Pat. No. 4,484,987, entitled "Method And Membrane Applicable To Implantable Sensor"; (2) U.S. Pat. No. 4,627,906, entitled "Electrochemical Sensor Having Improved Stability"; (3) U.S. Pat. No. 4,671,288, entitled "Electrochemical Cell Sensor For Continuous Short-Term Use In Tissues And Blood"; (4) U.S. Pat. No. 4,703,756, entitled "Complete Glucose Monitoring System With An Implantable Telemetered Sensor Module"; and (5) U.S. Pat. No. 4,781,798, entitled "Transparent Multi-Oxygen Sensor Array And Method Of Using Same". Each of these patents is incorporated herein by reference as if set forth in full.

Still further teachings concerning implantable sensors and sensor systems are found in a number of patents issued to J. H. Schulman, et al., including (1) U.S. Pat. No. 5,497,772, entitled "Glucose Monitoring System"; (2) U.S. Pat. No. 5,651,767, entitled "Replaceable Catheter System for Physiological Sensors, Stimulating Electrodes and/or Implantable Fluid Delivery Systems"; (3) U.S. Pat. No. 5,750,926, entitled "Hermetically Sealed Electrical Feedthrough For Use With Implantable Electronic Devices"; (4) U.S. Pat. No. 6,043,437, entitled "Alumina Insulation for Coating Implantable Components and Other Microminiature Devices"; (5) U.S. Pat. No. 6,088,608, entitled "Implantable Sensor and Integrity Test Therefor"; and (6) U.S. Pat. No. 6,119,028, entitled "Implantable Enzyme-Based Monitoring Systems Having Improved Longevity Due to Improved Exterior Surfaces". Each of these patents is incorporated herein by reference as if set forth in full.

Additional further teachings concerning implantable sensors and sensor systems are found in (1) U.S. Pat. No. 5,917,346, issued to J. C. Gord, et al., and entitled "Low power current-to-frequency converter"; (2) U.S. Pat. No. 5,999,848, issued to J. C. Gord, and entitled "Daisy Chainable Sensors for Implantation in Living Tissue"; (3) U.S. Pat. No. 5,999,849, issued to L. D. Canfield, et al., and entitled "Low Power Rectifier Circuit for Implantable Medical Devices"; and (4) U.S. Pat. No. 6,081,736, issued to M. S. Colvin, et al., and entitled "Implantable Enzyme-Based Monitoring Systems Adapted for Long Term Use". Each of these patents is incorporated herein by reference as if set forth in full.

Further teachings concerning implantable infusion pumps are found in a number of patents by R. E. Fischell, including (1) U.S. Pat. No. 4,373,527, entitled "Implantable, Programmable Medication Infusion System"; (2) U.S. Pat. No. 4,494,950, entitled "Infusion Device Intended for Implantation in a Living Body"; (3) U.S. Pat. No. 4,525,165, entitled "Fluid Handling System for Medication Infusion System"; (4) U.S. Pat. No. 4,573,994, entitled "Refillable Medication Infusion Apparatus"; (5) U.S. Pat. No. 4,594,058, entitled "Single Valve Diaphragm Pump with Decreased Sensitivity to Ambient Conditions"; (6) U.S. Pat. No. 4,619,653, entitled "Apparatus For Detecting At Least One Predetermined Condition And Providing An Informational Signal In Response Thereto In A Medication Infusion System"; (7) U.S. Pat. No. 4,661,097, entitled "Method for Clearing a Gas Bubble From a Positive Displacement Pump Contained Within a Fluid Dispensing System"; (8) U.S. Pat. No. 4,731,051, entitled "Programmable Control Means for Providing Safe and Controlled Medication Infusion"; and (9) U.S. Pat. No. 4,784,645, entitled, "Apparatus For Detecting A Condition Of A Medication Infusion System And Providing An Informational Signal In Response Thereto". Each of these patents is incorporated herein by reference as if set forth in full.

Still further teachings concerning infusion pumps are found in a number of patents by Franetzki, including (1) U.S. Pat. No. 4,191,181, entitled "Apparatus For Infusion of Liquids", (2) U.S. Pat. No. 4,217,894, entitled "Apparatus for Supplying Medication to the Human or Animal Body"; (3) U.S. Pat. No. 4,270,532, entitled "Device for the Pre-programmable Infusion of Liquids"; (4) U.S. Pat. No. 4,282,872, entitled "Device for the Pre-programmable Infusion of Liquids", U.S. Pat. No. 4,373,527, entitled "Implantable, Programmable Medication Infusion System"; (5) U.S. Pat. No. 4,511,355, entitled "Plural Module Medication Delivery System", (6) U.S. Pat. No. 4,559,037, entitled "Device for the Pre-programmable Infusion of Liquids"; (7) U.S. Pat.

No. 4,776,842, entitled "Device for the Administration of Medications". Each of these patents is incorporated herein by reference as if set forth in full.

Teachings concerning tissue stimulators are found in a number of patents by J. H. Schulman, including (1) U.S. Pat. No. 5,193,539, entitled "Implantable microstimulator"; (2) U.S. Pat. No. 5,193,540; entitled "Structure and Method of Manufacture of an Implantable Microstimulator"; and (3) U.S. Pat. No. 5,358,514, entitled "Implantable Microdevices with Self Attaching Electrodes". Further teachings are also found in (1) U.S. Pat. No. 5,957,958, by Loeb et al., entitled "Implantable nerve or muscle stimulator e.g. a cochlear prosthesis", in (2) U.S. Pat. No. 5,571,148, by G. E. Loeb, et al., entitled "Implantable Multichannel Stimulator"; and in (3) PCT Publication No. WO 00/74751, by A. E. Mann, and entitled "Method and Apparatus for Infusing Liquids Using a Chemical Reaction in an Implanted Infusion Device". Each of these publications is incorporated herein by reference as if set forth in full.

The control of an implantable sensor could be provided through the functionality of one or both Processor ICs. One Processor IC could supply power and/or control signals to the sensor(s) and receive data back from the sensor, while the other processor could monitor the activity to ensure that sensor activity meets certain predefined guidelines.

In other embodiments, the External Communication Device of the first embodiment could be functionally linked to an external glucose sensor system such as the continuous glucose monitoring system (CGMS) offered by Minimed Inc. of Northridge, Calif. The link may be established, for example, through a physical lead or by RF telemetry.

In other embodiments other implantable, or external, sensor systems that measure something other than glucose could also be functionally coupled to the implantable device either to receive power and/or to provide data. Other such sensors might include oxygen sensors, peroxide sensors, pulse rate sensors, temperature sensors, accelerometers, and the like.

In still other alternative embodiments, the electronic control system of the first embodiment could be configured to control one or more implantable sensors or is electrical stimulators with or without infusion functionality incorporated into the implantable device.

Further embodiments will be apparent to those of skill in the art upon review of the disclosure provided herein. Still further embodiments may be derived from the teachings set forth explicitly herein in combination with the teachings found in the various patent applications, publications, and patents referenced and incorporated herein.

While the description herein sets forth particular embodiments, it is believed that those of skill in the art will recognize many variations to the presented embodiments based on the teachings herein, as such it is believed that many additional modifications may be made without departing from the spirit of the teachings herein. The accompanying claims are intended to cover such modifications as would fall within the true scope and spirit of the present invention.

The disclosed embodiments are therefore to be considered as illustrative and not necessarily restrictive, the scope of the invention being indicated by the appended claims, rather than the foregoing description, and all changes which come within the meaning and range of equivalency of the claims are therefore intended to be embraced therein.

We claim:

1. A medical system, comprising:
   a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
   b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
   wherein the medical device further comprises an MD memory for holding an MD program that controls, at least in part, operation of the medical device,
   wherein the medical device is capable of executing a first type of software that allows communication with the communication device and also allows medically significant operations to occur,
   wherein the medical device is capable of executing a second type of software that allows communication with the communication device but does not allow medically significant operations to occur, and
   wherein a reset causes reloading of the second type of software from a non-volatile memory followed by reloading the first type of software from an external RAM into an internal RAM.

2. The system of claim 1 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

3. The system of claim 2 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

4. The system of claim 1 wherein the first and second types of software are incapable of executing simultaneously.

5. The system of claim 1 wherein the second type of software comprises bootloader software that executes upon powering up or resetting the medical device.

6. The system of claim 1 wherein the medical device is capable of receiving new software of the first type from a communication device when the medical device is executing the second type of software but not when executing the first type of software.

7. The system of claim 1 wherein the medical device is capable of receiving new software of the second type from a the communication device when the medical device is executing the second type of software but not when executing the first type of software.

8. The system of claim 1 wherein the medical device is capable of receiving a first type of telemetry communication, comprising at least a first message type, when the medical device is executing the second type of software and wherein the medical device is not capable of receiving the first type of telemetry communication when executing the first type of software.

9. The system of claim 1 wherein the medical device is capable of receiving a second type of telemetry communication, comprising at least a second message type, when the medical device is executing the first type of software and wherein the medical device is not capable of receiving the second type of telemetry communication when executing the second type of software.

10. The system of claim 1 wherein the medical device comprises an implantable infusion pump for selectively delivering a drug and wherein the infusion pump is capable of receiving commands related to at least one of (1) delivering selected amounts of the drug, or (2) delivering the drug at a selected rate.

11. The system of claim 1 wherein a copy of the software of the second type is stored in at least one non-volatile memory module that is connected to the at least one MD processor and wherein software in the at least one non-volatile memory module is executed upon power up or upon resetting of the medical device.

12. The system of claim 1 wherein the first type of software is stored in at least one non-volatile memory module that is connected to the at least one MD processor and wherein the software of the first type is loaded into a RAM module upon selective execution of the software of the second type.

13. The system of claim 1 wherein the first type of software is held in the medical device only in volatile RAM and must be reloaded after powering up or resetting the medical device.

14. The system of claim 1 wherein the at least one MD processor derives an error checking code for the software of the first type after transfer from a memory module in the communication device and compares the error checking code with an error checking code that was transferred with the software of the first type, wherein the software of the first type is only allowed to be executed when the error checking codes compare appropriately.

15. The system of claim 1 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose, or (5) an implantable electrode for selectively stimulating a portion of the body of the patient.

16. The system of claim 1, wherein the first or second type of software can be updated using a plurality of messages comprising a software message or a data message.

17. The system of claim 16 wherein each message of the plurality is sent with a validation code that is compared to a validation code that is derived, at least in part, from information received in the message, wherein the received and derived validation codes must appropriately compare for the received message to be considered valid.

18. The system of claim 17 wherein a validation code for an entire image is transmitted and compared to a validation code that is derived, at least in part, from the received and stored image, wherein the received and derived validation codes must appropriately compare for the received image to be considered valid.

19. A medical system, comprising:
a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
wherein the medical device further comprises an MD memory for holding an MD program that controls, at least in part, operation of the medical device,
wherein the medical device is capable of executing a first type of software that allows communication with the communication device and also allows medically significant operations to occur,
wherein the medical device is capable of executing a second type of software that allows communication with the communication device but does not allow medically significant operations to occur,
wherein the first or second type of software can be updated using a plurality of messages comprising a software message or a data message,
wherein each message of the plurality is sent with a validation code that is compared to a validation code that is derived, at least in part, from information received in the message,
wherein the received and derived validation codes must appropriately compare for the received message to be considered valid, and
wherein the plurality of messages transfer a software image.

20. A medical system, comprising:
a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and
b) a communication device (CD) comprising CD electronic control circuitry that further comprises at least one CD telemetry system and at least one CD processor that controls, at least in part, operation of the CD telemetry system and operation of the communication device,
wherein the CD telemetry system sends messages to or receives messages from the MD telemetry system,
wherein the medical device further comprises an MD memory for holding an MD program that controls, at least in part, operation of the medical device,
wherein the medical device is capable of executing a first type of software that allows communication with the communication device and also allows medically significant operations to occur,
wherein the medical device is capable of executing a second type of software that allows communication with the communication device hut does not allow medically significant operations to occur, wherein the first or second type of software can be updated using a plurality of messages comprising a software message or a data message, wherein each message of the plurality is sent with a validation code that is compared to a validation code that is derived, at least in part, from information received in the message, wherein the received and derived validation codes must appropriately compare for the received message to be considered valid, and wherein the plurality of messages transfer a data image.

21. A medical system, comprising:
a) an ambulatory medical device (MD) comprising MD electronic control circuitry that further comprises at least one MD telemetry system and at least one MD processor that controls, at least in part, operation of the MD telemetry system and Operation of the medical device, wherein the medical device is configured to provide a treatment to a body of a patient or to monitor a selected state of the body; and
b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system, wherein the medical device further comprises an MD memory for holding an MD program that controls, at least in part, operation of the medical device, wherein the medical device is capable of executing a first type of software that allows communication with the communication device and also allows medically significant operations to occur, wherein the medical device is capable of executing a second type of software that allows communication with the communication device but does not allow medically significant operations to occur, wherein the first or second type of software can be updated using a plurality of messages comprising a software message or a data message, wherein each message of the plurality is sent with a validation code that is compared to a validation code that is derived, at least in part, from information received in the message, wherein the received and derived validation codes must appropriately compare for the received message to be considered valid, and wherein the validation codes comprise CRCs.

* * * * *